US012753213B2

(12) United States Patent
Miyawaki et al.

(10) Patent No.: US 12,753,213 B2
(45) Date of Patent: Oct. 6, 2026

(54) POLYPEPTIDE EXHIBITING FLUORESCENT PROPERTIES AND USE FOR SAME

(71) Applicants: RIKEN, Saitama (JP); TOHOKU UNIVERSITY, Miyagi (JP)

(72) Inventors: Atsushi Miyawaki, Saitama (JP); Ryoko Ando, Saitama (JP); Masahiko Hirano, Saitama (JP); Noriyo Takeda, Miyagi (JP)

(73) Assignees: RIKEN, Saitama (JP); TOHOKU UNIVERSITY, Miyagi (JP)

( * ) Notice: Subject to any disclaimer, the term of this patent is extended or adjusted under 35 U.S.C. 154(b) by 450 days.

(21) Appl. No.: 18/285,732

(22) PCT Filed: Mar. 23, 2022

(86) PCT No.: PCT/JP2022/013700
§ 371 (c)(1),
(2) Date: Oct. 5, 2023

(87) PCT Pub. No.: WO2022/215532
PCT Pub. Date: Oct. 13, 2022

(65) Prior Publication Data

US 2024/0209039 A1 Jun. 27, 2024

(30) Foreign Application Priority Data

Apr. 7, 2021 (JP) ................................ 2021-065373

(51) Int. Cl.

*C07K 14/435* (2006.01)
*C12N 15/70* (2006.01)
*C12N 15/86* (2006.01)
*G01N 33/58* (2006.01)

(52) U.S. Cl.

CPC ........ *C07K 14/43595* (2013.01); *C12N 15/70* (2013.01); *C12N 15/86* (2013.01); *G01N 33/582* (2013.01); *C07K 2319/60* (2013.01); *C12N 2740/15041* (2013.01)

(58) Field of Classification Search

CPC ................................................ C07K 14/43536
See application file for complete search history.

(56) References Cited

U.S. PATENT DOCUMENTS

| | | | |
|---|---|---|---|
| 2006/0167225 | A1 | 7/2006 | Gurskaya |
| 2007/0298412 | A1 | 12/2007 | Lukyanov et al. |
| 2017/0081371 | A1 | 3/2017 | Minshull et al. |
| 2019/0085039 | A1 | 3/2019 | Nagai et al. |

FOREIGN PATENT DOCUMENTS

| | | |
|---|---|---|
| JP | 2005-526495 | 9/2005 |
| JP | 2006-506100 | 2/2006 |
| WO | WO 2017-155101 | 9/2017 |

OTHER PUBLICATIONS

Office Action for JP Patent Application No. 2023-512930, dated Sep. 2, 2025, 9 pages.
Database Geneseq [Online] May 4, 2017 (May 4, 2017), "*E. coli* chromo- or fluorescent protein, SEQ ID 34.", XP002812977, retrieved from EBI accession No. GSPzBDS66523 Database accession No. BDS66523
Prudkovsky Andrey A. et al: "Green Fluorescence of Cytaeis Hydroids Living in Association with Nassarius Gastropods in the Red Sea", PLOS ONE, vol. 11, No. 2, E0146861, Feb. 3, 2016 (Feb. 3, 2016), pp. 1-10, XP093248453, US ISSN: 1932-6203, DOI:10.1371/journal.pone.0146861
Hirano Masahiko et al: "A highly photostable and bright green fluorescent protein", Nature Biotechnology, Nature Publishing Group US, New York, vol. 40, No. 7, Apr. 25, 2022 (Apr. 25, 2022) , pp. 1132-1142, XP037903041, ISSN: 1087-0156, DOI: 10.1038/841587-022-01278-2 [retrieved on Apr. 25, 2022].
Extended European Search Report, EP Patent Application No. 227845179, dated Feb. 21, 2025, 7 pages.
Shaner, N. C. et al., Nature Methods 5, pp. 545-551, 2008.
Shaner, N. C., Methods in Cell Biology 123, pp. 95-111,2014.
Bindels, D. S. et al. Nature Methods 14, pp. 53-56, 2017.
Zhong, S. et al. Journal of Neuroscience Methods 313, pp. 68-76, 2019.
Shaner, N.C. et al. Nature Methods 10, pp. 407-409, 2013.
Deguchi, Ryusaku et al. Green fluorescent protein (GFP)-like substance . . . Miyagi University of Education. 2012, vol. 47, pp. 95-100 (in particular, summary, section "5. Conclusion").
International Search Report for PCT/JP2022/013700 and its English translation, dated Jun. 14, 2022, 8 pages.
Written Opinion for PCT/JP2022/013700 and its English translation (International Preliminary Report on Patentability), dated Jun. 14, 2022, 8 pages.

*Primary Examiner* — Suzanne M Noakes
(74) *Attorney, Agent, or Firm* — Casimir Jones, S.C.; Robert A. Goetz

(57) ABSTRACT

A novel fluorescent protein and uses thereof are provided. A polypeptide of the present invention has a fluorescence property, the polypeptide being indicated in any one of (1) to (3) below: (1) a polypeptide having an amino acid sequence set forth in SEQ ID NO: 1; (2) a polypeptide having an amino acid sequence set forth in SEQ ID NO: 1, the amino acid sequence having replaced, deleted, inserted, and/or added therein not less than 1 and not more than 32 amino acids; and (3) a polypeptide having not less than 85% sequence identity with respect to an amino acid sequence set forth in SEQ ID NO: 1.

13 Claims, 10 Drawing Sheets

Specification includes a Sequence Listing.

FIG. 4

```
                              ***
CU17S     MAS------- --TPFKFQLK GTINGKSFTV EGEGEGNSHE GSHKGKYVCT   41
StayGold  MAS------- --TPFKFQLK GTINGKSFTV EGEGEGNSHE GSHKGKYVCT   41
EGFP      MVSKGEELFT GVVPILVELD GDVNGHKFSV SGEGEGDATY GKLTLKFICT   50

                          ***
CU17S     SGKLPMSWAA LGTSFGYGMK YYTKYPSGLK --NWFHEVMP EGFTYDRHIQ   89
StayGold  SGKLPMSWAA LGTSFGYGMK YYTKYPSGLK --NWFHEVMP EGFTYDRHIQ   89
EGFP      TGKLPVPWPT LVTTLTYGVQ CFSRYPDHMK QHDFFKSAMP EGYVQERTIF  100

CU17S     YKGDGSIHAK HQHFMKNGTY HNIVEFTGQD FKENSPVLTG DMNVSLPNEV  139
StayGold  YKGDGSIHAK HQHFMKNGTY HNIVEFTGQD FKENSPVLTG DMNVSLPNEV  139
EGFP      FKDDGNYKTR AEVKFEGDTL VNRIELKGID FKEDGNILGH KLEYNYNSHN  150

CU17S     QHIPRD---D GVECPVTLLY PLLSDKSKCV EVHQNTICKP LHNQPAPDVP  186
StayGold  QHIPRD---D GVECPVTLLY PLLSDKSKCV EAHQNTICKP LHNQPAPDVP  186
EGFP      VYIMADKQKN GIKVNFKIRH NIEDGSVQLA DHYQQNT--P IGDGPVLLPD  198

CU17S     YHWIRKQYTQ SKDDTEERDH ICQSETLEAH L--------- -.........  217
StayGold  YHWIRKQYTQ SKDDTEERDH ICQSETLEAH L--------- -.........  217
EGFP      NHYLSTQSAL SKDPNEKRDH MVLLEFVTAA GITLGMDELY K.........  239
```

FIG. 5

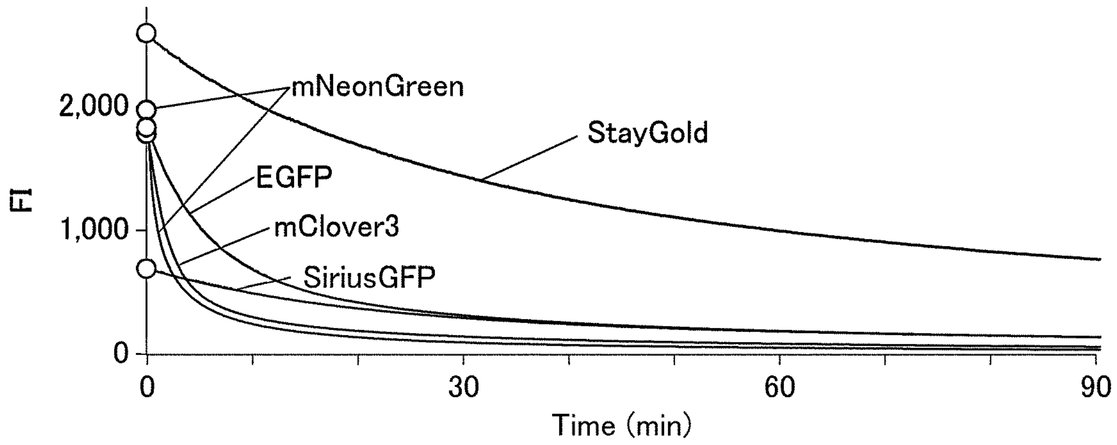

SEQUENCE LISTING

```
<160> NUMBER OF SEQ ID NOS: 33

<210> SEQ ID NO 1
<211> LENGTH: 217
<212> TYPE: PRT
<213> ORGANISM: Cytaeis uchidae

<400> SEQUENCE: 1

Met Ala Ser Thr Pro Phe Lys Phe Gln Leu Lys Gly Thr Ile Asn Gly
1               5                   10                  15

Lys Ser Phe Thr Val Glu Gly Glu Gly Glu Gly Asn Ser His Glu Gly
            20                  25                  30
```

```
Ser His Lys Gly Lys Tyr Val Cys Thr Ser Gly Lys Leu Pro Met Ser
        35                  40                  45

Trp Ala Ala Leu Gly Thr Ser Phe Gly Tyr Gly Met Lys Tyr Tyr Thr
    50                  55                  60

Lys Tyr Pro Ser Gly Leu Lys Asn Trp Phe His Glu Val Met Pro Glu
65                  70                  75                  80

Gly Phe Thr Tyr Asp Arg His Ile Gln Tyr Lys Gly Asp Gly Ser Ile
                85                  90                  95

His Ala Lys His Gln His Phe Met Lys Asn Gly Thr Tyr His Asn Ile
            100                 105                 110

Val Glu Phe Thr Gly Gln Asp Phe Lys Glu Asn Ser Pro Val Leu Thr
        115                 120                 125

Gly Asp Met Asn Val Ser Leu Pro Asn Glu Val Gln His Ile Pro Arg
    130                 135                 140

Asp Asp Gly Val Glu Cys Pro Val Thr Leu Leu Tyr Pro Leu Leu Ser
145                 150                 155                 160

Asp Lys Ser Lys Cys Val Glu Ala His Gln Asn Thr Ile Cys Lys Pro
                165                 170                 175

Leu His Asn Gln Pro Ala Pro Asp Val Pro Tyr His Trp Ile Arg Lys
            180                 185                 190

Gln Tyr Thr Gln Ser Lys Asp Asp Thr Glu Glu Arg Asp His Ile Cys
        195                 200                 205

Gln Ser Glu Thr Leu Glu Ala His Leu
    210                 215
```

<210> SEQ ID NO 2
<211> LENGTH: 654
<212> TYPE: DNA
<213> ORGANISM: Cytaeis uchidae

<400> SEQUENCE: 2

```
atggctagta caccatttaa atttcaactt aaaggaacca tcaatggcaa atcgtttacc      60

gttgaaggcg aaggtgaagg aaattcacat gaaggttctc ataaaggaaa atatgtttgt     120

acaagtggaa aactaccgat gtcatgggca gcacttggaa catcctttgg ttatggaatg     180

aaatattata ccaaatatcc tagtggactg aagaactggt ttcatgaagt aatgcctgaa     240

ggctttacct acgatcgtca tattcaatat aaaggcgatg ggagtatcca tgcaaaacac     300

caacacttta tgaaaaatgg gacttatcac aacattgttg aatttactgg tcaggatttt     360

aaagaaaata gtccagtctt aactggagat atgaatgtct cattaccgaa tgaagttcaa     420

catataccca gagatgatgg agtagaatgc ccagtgacct tgctttatcc tttattatcg     480

gataaatcaa aatgcgttga ggctcaccaa aatacaatct gcaagcctct tcataatcaa     540

ccagcacctg atgtcccata tcactggatt cgtaaacaat acacacaaag caaagatgat     600

accgaggaac gtgatcatat ttgtcaatca gagactctcg aagcacactt ataa           654
```

<210> SEQ ID NO 3
<211> LENGTH: 654
<212> TYPE: DNA
<213> ORGANISM: Cytaeis uchidae

<400> SEQUENCE: 3

```
atggccagca ccccccttcaa gttccagctg aagggcacca tcaacggcaa gagcttcacc      60

gtggaaggcg agggcgaggg caatagccac gagggcagcc acaaaggcaa gtacgtgtgc     120

accagcggca aactgccaat gtcttgggcc gccctgggaa ctagcttcgg ctatggcatg     180
```

```
aagtactaca ccaagtaccc cagcggcctg aagaactggt tccacgaggt gatgcccgag    240

ggcttcacct acgacagaca catccagtac aagggcgacg gcagcatcca cgccaagcac    300

cagcacttca tgaagaacgg cacctaccac aacatcgtgg agttcaccgg ccaggacttc    360

aaggagaaca gccccgtgct gaccggcgac atgaacgtga gcctgcccaa cgaggtgcag    420

cacatcccca gagatgacgg cgtggagtgc ccagtgaccc tgctgtaccc tctgctgagc    480

gacaagagca agtgcgtgga ggcccaccag aacaccatct gcaagcccct gcacaatcag    540

ccagcccccg atgtgccata ccactggatc agaaagcagt acacccagag caaggacgac    600

accgaggaga gagaccacat ctgccagagc gagaccctgg aggcccacct gtaa          654
```

```
<210> SEQ ID NO 4
<211> LENGTH: 217
<212> TYPE: PRT
<213> ORGANISM: Cytaeis uchidae

<400> SEQUENCE: 4

Met Ala Ser Thr Pro Phe Lys Phe Gln Leu Lys Gly Thr Ile Asn Gly
1               5                   10                  15

Lys Ser Phe Thr Val Glu Gly Glu Gly Glu Gly Asn Ser His Glu Gly
            20                  25                  30

Ser His Lys Gly Lys Tyr Val Cys Thr Ser Gly Lys Leu Pro Met Ser
        35                  40                  45

Trp Ala Ala Leu Gly Thr Ser Phe Gly Tyr Gly Met Lys Tyr Tyr Thr
    50                  55                  60

Lys Tyr Pro Ser Gly Leu Lys Asn Trp Phe His Glu Val Met Pro Glu
65                  70                  75                  80

Gly Phe Thr Tyr Asp Arg His Ile Gln Tyr Lys Gly Asp Gly Ser Ile
                85                  90                  95

His Ala Lys His Gln His Phe Met Lys Asn Gly Thr Tyr His Asn Ile
            100                 105                 110

Val Glu Phe Thr Gly Gln Asp Phe Lys Glu Asn Ser Pro Val Leu Thr
        115                 120                 125

Gly Asp Met Asn Val Ser Leu Pro Asn Glu Val Gln His Ile Pro Arg
    130                 135                 140

Asp Asp Gly Val Glu Cys Pro Val Thr Leu Leu Tyr Pro Leu Leu Ser
145                 150                 155                 160

Asp Lys Ser Lys Cys Val Glu Val His Gln Asn Thr Ile Cys Lys Pro
                165                 170                 175

Leu His Asn Gln Pro Ala Pro Asp Val Pro Tyr His Trp Ile Arg Lys
            180                 185                 190

Gln Tyr Thr Gln Ser Lys Asp Asp Thr Glu Glu Arg Asp His Ile Cys
        195                 200                 205

Gln Ser Glu Thr Leu Glu Ala His Leu
    210                 215


<210> SEQ ID NO 5
<211> LENGTH: 654
<212> TYPE: DNA
<213> ORGANISM: Cytaeis uchidae

<400> SEQUENCE: 5

atggctagta caccatttaa atttcaactt aaaggaacca tcaatggcaa atcgtttacc     60

gttgaaggcg aaggtgaagg aaattcacat gaaggttctc ataaaggaaa atatgtttgt    120
```

```
acaagtggaa aactaccgat gtcatgggca gcacttggaa catcctttgg ttatggaatg    180

aaatattata ccaaatatcc tagtggactg aagaactggt ttcatgaagt aatgcctgaa    240

ggctttacct acgatcgtca tattcaatat aaaggcgatg ggagtatcca tgcaaaacac    300

caacacttta tgaaaaatgg gacttatcac aacattgttg aatttactgg tcaggatttt    360

aaagaaaata gtccagtctt aactggagat atgaatgtct cattaccgaa tgaagttcaa    420

catataccca gagatgatgg agtagaatgc ccagtgacct tgctttatcc tttattatcg    480

gataaatcaa aatgcgttga ggttcaccaa aatacaatct gcaagcctct tcataatcaa    540

ccagcacctg atgtcccata tcactggatt cgtaaacaat acacacaaag caaagatgat    600

accgaggaac gtgatcatat ttgtcaatca gagactctcg aagcacactt ataa          654


<210> SEQ ID NO 6
<211> LENGTH: 217
<212> TYPE: PRT
<213> ORGANISM: Cytaeis uchidae

<400> SEQUENCE: 6

Met Ala Ser Thr Pro Phe Lys Phe Gln Leu Lys Gly Thr Ile Asn Gly
1               5                   10                  15

Lys Ser Phe Thr Val Glu Gly Glu Gly Glu Gly Asn Ser His Glu Gly
            20                  25                  30

Ser His Lys Gly Lys Tyr Val Cys Thr Ser Gly Lys Leu Pro Met Ser
        35                  40                  45

Trp Ala Ala Leu Gly Thr Ser Phe Gly Tyr Gly Met Lys Tyr Tyr Thr
    50                  55                  60

Lys Tyr Pro Ser Gly Leu Lys Asn Trp Phe His Glu Val Met Pro Glu
65                  70                  75                  80

Gly Phe Thr Tyr Asp Arg His Ile Gln Tyr Lys Gly Asp Gly Ser Ile
                85                  90                  95

His Ala Lys His Gln His Phe Met Lys Asn Gly Thr Tyr His Asn Ile
            100                 105                 110

Val Glu Phe Thr Gly Gln Asp Phe Lys Glu Asn Ser Pro Val Leu Thr
        115                 120                 125

Gly Asp Met Asn Val Ser Leu Pro Asn Glu Val Gln His Ile Pro Arg
    130                 135                 140

Asp Asp Gly Val Glu Cys Pro Val Thr Leu Leu Tyr Pro Leu Leu Ser
145                 150                 155                 160

Asp Lys Ser Lys Cys Val Glu Ala Tyr Gln Asn Thr Ile Ile Lys Pro
                165                 170                 175

Leu His Asn Gln Pro Ala Pro Asp Val Pro Tyr His Trp Ile Arg Lys
            180                 185                 190

Gln Tyr Thr Gln Ser Lys Asp Asp Thr Glu Glu Arg Asp His Ile Ile
        195                 200                 205

Gln Ser Glu Thr Leu Glu Ala His Leu
    210                 215


<210> SEQ ID NO 7
<211> LENGTH: 654
<212> TYPE: DNA
<213> ORGANISM: Cytaeis uchidae

<400> SEQUENCE: 7

atggctagta caccatttaa atttcaactt aaaggaacca tcaatggcaa atcgtttacc     60

gttgaaggcg aaggtgaagg aaattcacat gaaggttctc ataaaggaaa atatgtttgt    120
```

```
acaagtggaa aactaccgat gtcatgggca gcacttggaa catcctttgg ttatggaatg    180

aaatattata ccaaatatcc tagtggactg aagaactggt ttcatgaagt aatgcctgaa    240

ggctttacct acgatcgtca tattcaatat aaaggcgatg ggagtatcca tgcaaaacac    300

caacacttta tgaaaaatgg gacttatcac aacattgttg aatttactgg tcaggatttt    360

aaagaaaata gtccagtctt aactggagat atgaatgtct cattaccgaa tgaagttcaa    420

catataccca gagatgatgg agtagaatgc ccagtgacct tgctttatcc tttattatcg    480

gataaatcaa aatgcgttga ggcttaccaa aatacaatca tcaagcctct tcataatcaa    540

ccagcacctg atgtcccata tcactggatt cgtaaacaat acacacaaag caaagatgat    600

accgaggaac gtgatcatat tattcaatca gagactctcg aagcacactt ataa          654
```

<210> SEQ ID NO 8
<211> LENGTH: 10
<212> TYPE: PRT
<213> ORGANISM: Artificial Sequence
<220> FEATURE:
<223> OTHER INFORMATION: c4

<400> SEQUENCE: 8

```
Pro Trp His Glu Pro Ser Ala Ser Ala Val
1               5                   10
```

<210> SEQ ID NO 9
<211> LENGTH: 9
<212> TYPE: PRT
<213> ORGANISM: Artificial Sequence
<220> FEATURE:
<223> OTHER INFORMATION: n1

<400> SEQUENCE: 9

```
Gly Glu Glu Leu Phe Thr Gly Val Val
1               5
```

<210> SEQ ID NO 10
<211> LENGTH: 9
<212> TYPE: PRT
<213> ORGANISM: Artificial Sequence
<220> FEATURE:
<223> OTHER INFORMATION: n2

<400> SEQUENCE: 10

```
Lys Gly Glu Glu Leu Phe Thr Gly Val
1               5
```

<210> SEQ ID NO 11
<211> LENGTH: 28
<212> TYPE: DNA
<213> ORGANISM: Artificial Sequence
<220> FEATURE:
<223> OTHER INFORMATION: 174C>I Primer

<400> SEQUENCE: 11

```
caccaaaata caatcatcaa gcctcttc                                        28
```

<210> SEQ ID NO 12
<211> LENGTH: 28
<212> TYPE: DNA
<213> ORGANISM: Artificial Sequence
<220> FEATURE:
<223> OTHER INFORMATION: 208C>I Primer

<400> SEQUENCE: 12
cgtgatcata ttattcaatc agagactc 28

<210> SEQ ID NO 13
<211> LENGTH: 582
<212> TYPE: PRT
<213> ORGANISM: Cytaeis uchidae

<400> SEQUENCE: 13

Met Val Ser Thr Gly Glu Glu Leu Phe Thr Gly Val Val Pro Phe Lys
1 5 10 15

Phe Gln Leu Lys Gly Thr Ile Asn Gly Lys Ser Phe Thr Val Glu Gly
20 25 30

Glu Gly Glu Gly Asn Ser His Glu Gly Ser His Lys Gly Lys Tyr Val
35 40 45

Cys Thr Ser Gly Lys Leu Pro Met Ser Trp Ala Ala Leu Gly Thr Ser
50 55 60

Phe Gly Tyr Gly Met Lys Tyr Tyr Thr Lys Tyr Pro Ser Gly Leu Lys
65 70 75 80

Asn Trp Phe His Glu Val Met Pro Glu Gly Phe Thr Tyr Asp Arg His
85 90 95

Ile Gln Tyr Lys Gly Asp Gly Ser Ile His Ala Lys His Gln His Phe
100 105 110

Met Lys Asn Gly Thr Tyr His Asn Ile Val Glu Phe Thr Gly Gln Asp
115 120 125

Phe Lys Glu Asn Ser Pro Val Leu Thr Gly Asp Met Asn Val Ser Leu
130 135 140

Pro Asn Glu Val Gln His Ile Pro Arg Asp Asp Gly Val Glu Cys Pro
145 150 155 160

Val Thr Leu Leu Tyr Pro Leu Leu Ser Asp Lys Ser Lys Cys Val Glu
165 170 175

Ala His Gln Asn Thr Ile Cys Lys Pro Leu His Asn Gln Pro Ala Pro
180 185 190

Asp Val Pro Tyr His Trp Ile Arg Lys Gln Tyr Thr Gln Ser Lys Asp
195 200 205

Asp Thr Glu Glu Arg Asp His Ile Cys Gln Ser Glu Thr Leu Glu Ala
210 215 220

His Leu Pro Trp His Glu Pro Ser Ala Ser Ala Val Glu Phe Ser Ala
225 230 235 240

Gly Gly Ser Ala Gly Gly Ser Ala Gly Gly Ser Ala Gly Gly Ser Ala
245 250 255

Gly Gly Ser Gly Ser Ala Gly Gly Ser Ala Gly Gly Ser Thr Ser Ala
260 265 270

Gly Gly Ser Ala Gly Gly Ser Ala Gly Gly Ser Ala Gly Gly Ser Ala
275 280 285

Gly Gly Ser Gly Ser Ala Gly Gly Ser Ala Gly Gly Ser Thr Ser Ala
290 295 300

Gly Gly Ser Ala Gly Gly Ser Ala Gly Gly Ser Ala Gly Gly Ser Ala
305 310 315 320

Gly Gly Ser Gly Ser Ala Gly Gly Ser Ala Gly Gly Ser Thr Ser Ala
325 330 335

Gly Gly Ser Ala Gly Gly Ser Ala Gly Gly Ser Ala Gly Gly Ser Ala
340 345 350

```
Gly Gly Lys Leu Met Val Ser Thr Gly Glu Glu Leu Phe Thr Gly Val
        355                 360                 365

Val Pro Phe Lys Phe Gln Leu Lys Gly Thr Ile Asn Gly Lys Ser Phe
    370                 375                 380

Thr Val Glu Gly Glu Gly Glu Gly Asn Ser His Glu Gly Ser His Lys
385                 390                 395                 400

Gly Lys Tyr Val Cys Thr Ser Gly Lys Leu Pro Met Ser Trp Ala Ala
                405                 410                 415

Leu Gly Thr Ser Phe Gly Tyr Gly Met Lys Tyr Tyr Thr Lys Tyr Pro
            420                 425                 430

Ser Gly Leu Lys Asn Trp Phe His Glu Val Met Pro Glu Gly Phe Thr
        435                 440                 445

Tyr Asp Arg His Ile Gln Tyr Lys Gly Asp Gly Ser Ile His Ala Lys
    450                 455                 460

His Gln His Phe Met Lys Asn Gly Thr Tyr His Asn Ile Val Glu Phe
465                 470                 475                 480

Thr Gly Gln Asp Phe Lys Glu Asn Ser Pro Val Leu Thr Gly Asp Met
                485                 490                 495

Asn Val Ser Leu Pro Asn Glu Val Gln His Ile Pro Arg Asp Asp Gly
            500                 505                 510

Val Glu Cys Pro Val Thr Leu Leu Tyr Pro Leu Leu Ser Asp Lys Ser
        515                 520                 525

Lys Cys Val Glu Ala His Gln Asn Thr Ile Cys Lys Pro Leu His Asn
    530                 535                 540

Gln Pro Ala Pro Asp Val Pro Tyr His Trp Ile Arg Lys Gln Tyr Thr
545                 550                 555                 560

Gln Ser Lys Asp Asp Thr Glu Glu Arg Asp His Ile Cys Gln Ser Glu
                565                 570                 575

Thr Leu Glu Ala His Leu
            580


<210> SEQ ID NO 14
<211> LENGTH: 1746
<212> TYPE: DNA
<213> ORGANISM: Cytaeis uchidae

<400> SEQUENCE: 14

atggtgtcta caggcgagga gctgtttacc ggcgtggtgc ccttcaagtt ccagctgaag     60

ggcaccatca acggcaagag cttcaccgtg gaaggcgagg gcgagggcaa tagccacgag    120

ggcagccaca aaggcaagta cgtgtgcacc agcggcaaac tgccaatgtc ttgggccgcc    180

ctgggaacta gcttcggcta tggcatgaag tactacacca agtaccccag cggcctgaag    240

aactggttcc acgaggtgat gcccgagggc ttcacctacg acagacacat ccagtacaag    300

ggcgacggca gcatccacgc caagcaccag cacttcatga agaacggcac ctaccacaac    360

atcgtggagt tcaccggcca ggacttcaag gagaacagcc ccgtgctgac cggcgacatg    420

aacgtgagcc tgcccaacga ggtgcagcac atccccagag atgacggcgt ggagtgccca    480

gtgaccctgc tgtaccctct gctgagcgac aagagcaagt gcgtggaggc ccaccagaac    540

accatctgca agcccctgca caatcagcca gcccccgatg tgccatacca ctggatcaga    600

aagcagtaca cccagagcaa ggacgacacc gaggagagag accacatctg ccagagcgag    660

accctggagg cccacctgcc atggcacgag ccttctgctt ctgccgtgga attcagtgct    720

ggtggttctg ctggaggaag cgccggaggt tccgctgggg gaagcgcagg cggctccggc    780
```

```
agcgctggcg ggagtgccgg gggcagtacc tccgcaggag gaagtgcagg gggaagcgct    840

ggtggcagtg cggggggttc cgcaggcggt agcggttccg ccggtggatc tgccggtgga    900

agcacatctg ctgggggtag tgcaggaggg tccgctggtg ggagcgcagg tggatctgcc    960

ggggggtctg gaagtgcagg tggtagcgct ggagggtcca catctgcagg tgggtctgct   1020

ggcggttccg ccggagggag tgccggcggt agcgccggtg ggaagcttat ggtgagtaca   1080

ggggaggagc tgttcaccgg ggtggtgcca tttaaatttc aacttaaagg aaccatcaat   1140

ggcaaatcgt ttaccgttga aggcgaaggt gaaggaaatt cacatgaagg ttctcataaa   1200

ggaaaatatg tttgtacaag tggaaaacta ccgatgtcat gggcagcact tggaacatcc   1260

tttggttatg gaatgaaata ttataccaaa tatcctagtg gactgaagaa ctggtttcat   1320

gaagtaatgc ctgaaggctt tacctacgat cgtcatattc aatataaagg cgatgggagt   1380

atccatgcaa aacaccaaca ctttatgaaa aatgggactt atcacaacat tgttgaattt   1440

actggtcagg attttaaaga aaatagtcca gtcttaactg gagatatgaa tgtctcatta   1500

ccgaatgaag ttcaacatat acccagagat gatggagtag aatgcccagt gaccttgctt   1560

tatcctttat tatcggataa atcaaaatgc gttgaggctc accaaaatac aatctgcaag   1620

cctcttcata atcaaccagc acctgatgtc ccatatcact ggattcgtaa acaatacaca   1680

caaagcaaag atgataccga ggaacgtgat catatttgtc aatcagagac tctcgaagca   1740

cactta                                                              1746
```

<210> SEQ ID NO 15
<211> LENGTH: 592
<212> TYPE: PRT
<213> ORGANISM: Cytaeis uchidae

<400> SEQUENCE: 15

```
Met Val Ser Thr Gly Glu Glu Leu Phe Thr Gly Val Val Pro Phe Lys
1               5                   10                  15

Phe Gln Leu Lys Gly Thr Ile Asn Gly Lys Ser Phe Thr Val Glu Gly
            20                  25                  30

Glu Gly Glu Gly Asn Ser His Glu Gly Ser His Lys Gly Lys Tyr Val
        35                  40                  45

Cys Thr Ser Gly Lys Leu Pro Met Ser Trp Ala Ala Leu Gly Thr Ser
    50                  55                  60

Phe Gly Tyr Gly Met Lys Tyr Tyr Thr Lys Tyr Pro Ser Gly Leu Lys
65                  70                  75                  80

Asn Trp Phe His Glu Val Met Pro Glu Gly Phe Thr Tyr Asp Arg His
                85                  90                  95

Ile Gln Tyr Lys Gly Asp Gly Ser Ile His Ala Lys His Gln His Phe
            100                 105                 110

Met Lys Asn Gly Thr Tyr His Asn Ile Val Glu Phe Thr Gly Gln Asp
        115                 120                 125

Phe Lys Glu Asn Ser Pro Val Leu Thr Gly Asp Met Asn Val Ser Leu
    130                 135                 140

Pro Asn Glu Val Gln His Ile Pro Arg Asp Asp Gly Val Glu Cys Pro
145                 150                 155                 160

Val Thr Leu Leu Tyr Pro Leu Leu Ser Asp Lys Ser Lys Cys Val Glu
                165                 170                 175

Ala His Gln Asn Thr Ile Cys Lys Pro Leu His Asn Gln Pro Ala Pro
            180                 185                 190
```

```
Asp Val Pro Tyr His Trp Ile Arg Lys Gln Tyr Thr Gln Ser Lys Asp
        195                 200                 205

Asp Thr Glu Glu Arg Asp His Ile Cys Gln Ser Glu Thr Leu Glu Ala
    210                 215                 220

His Leu Pro Trp His Glu Pro Ser Ala Ser Ala Val Glu Phe Ser Ala
225                 230                 235                 240

Gly Gly Ser Ala Gly Gly Ser Ala Gly Gly Ser Ala Gly Gly Ser Ala
                245                 250                 255

Gly Gly Ser Gly Ser Ala Gly Gly Ser Ala Gly Gly Ser Thr Ser Ala
            260                 265                 270

Gly Gly Ser Ala Gly Gly Ser Ala Gly Gly Ser Ala Gly Gly Ser Ala
        275                 280                 285

Gly Gly Ser Gly Ser Ala Gly Gly Ser Ala Gly Gly Ser Thr Ser Ala
    290                 295                 300

Gly Gly Ser Ala Gly Gly Ser Ala Gly Gly Ser Ala Gly Gly Ser Ala
305                 310                 315                 320

Gly Gly Ser Gly Ser Ala Gly Gly Ser Ala Gly Gly Ser Thr Ser Ala
                325                 330                 335

Gly Gly Ser Ala Gly Gly Ser Ala Gly Gly Ser Ala Gly Gly Ser Ala
            340                 345                 350

Gly Gly Lys Leu Met Val Ser Thr Gly Glu Glu Leu Phe Thr Gly Val
        355                 360                 365

Val Pro Phe Lys Phe Gln Leu Lys Gly Thr Ile Asn Gly Lys Ser Phe
    370                 375                 380

Thr Val Glu Gly Glu Gly Glu Gly Asn Ser His Glu Gly Ser His Lys
385                 390                 395                 400

Gly Lys Tyr Val Cys Thr Ser Gly Lys Leu Pro Met Ser Trp Ala Ala
                405                 410                 415

Leu Gly Thr Ser Phe Gly Tyr Gly Met Lys Tyr Tyr Thr Lys Tyr Pro
            420                 425                 430

Ser Gly Leu Lys Asn Trp Phe His Glu Val Met Pro Glu Gly Phe Thr
        435                 440                 445

Tyr Asp Arg His Ile Gln Tyr Lys Gly Asp Gly Ser Ile His Ala Lys
    450                 455                 460

His Gln His Phe Met Lys Asn Gly Thr Tyr His Asn Ile Val Glu Phe
465                 470                 475                 480

Thr Gly Gln Asp Phe Lys Glu Asn Ser Pro Val Leu Thr Gly Asp Met
                485                 490                 495

Asn Val Ser Leu Pro Asn Glu Val Gln His Ile Pro Arg Asp Asp Gly
            500                 505                 510

Val Glu Cys Pro Val Thr Leu Leu Tyr Pro Leu Leu Ser Asp Lys Ser
        515                 520                 525

Lys Cys Val Glu Ala His Gln Asn Thr Ile Cys Lys Pro Leu His Asn
    530                 535                 540

Gln Pro Ala Pro Asp Val Pro Tyr His Trp Ile Arg Lys Gln Tyr Thr
545                 550                 555                 560

Gln Ser Lys Asp Asp Thr Glu Glu Arg Asp His Ile Cys Gln Ser Glu
                565                 570                 575

Thr Leu Glu Ala His Leu Pro Trp His Glu Pro Ser Ala Ser Ala Val
            580                 585                 590
```

<210> SEQ ID NO 16
<211> LENGTH: 1776

```
<212> TYPE: DNA
<213> ORGANISM: Cytaeis uchidae

<400> SEQUENCE: 16

atggtgtcta caggcgagga gctgtttacc ggcgtggtgc ccttcaagtt ccagctgaag     60
ggcaccatca acggcaagag cttcaccgtg gaaggcgagg gcgagggcaa tagccacgag    120
ggcagccaca aaggcaagta cgtgtgcacc agcggcaaac tgccaatgtc ttgggccgcc    180
ctgggaacta gcttcggcta tggcatgaag tactacacca agtaccccag cggcctgaag    240
aactggttcc acgaggtgat gcccgagggc ttcacctacg acagacacat ccagtacaag    300
ggcgacggca gcatccacgc caagcaccag cacttcatga agaacggcac ctaccacaac    360
atcgtggagt tcaccggcca ggacttcaag gagaacagcc ccgtgctgac cggcgacatg    420
aacgtgagcc tgcccaacga ggtgcagcac atccccagag atgacggcgt ggagtgccca    480
gtgaccctgc tgtaccctct gctgagcgac aagagcaagt gcgtggaggc ccaccagaac    540
accatctgca agcccctgca caatcagcca gcccccgatg tgccatacca ctggatcaga    600
aagcagtaca cccagagcaa ggacgacacc gaggagagag accacatctg ccagagcgag    660
accctggagg cccacctgcc atggcacgag ccttctgctt ctgccgtgga attcagtgct    720
ggtggttctg ctggaggaag cgccggaggt tccgctgggg gaagcgcagg cggctccggc    780
agcgctggcg ggagtgccgg gggcagtacc tccgcaggag gaagtgcagg gggaagcgct    840
ggtggcagtg cggggggttc cgcaggcggt agcggttccg ccggtggatc tgccggtgga    900
agcacatctg ctgggggtag tgcaggaggg tccgctggtg ggagcgcagg tggatctgcc    960
ggggggtctg gaagtgcagg tggtagcgct ggagggtcca catctgcagg tgggtctgct   1020
ggcggttccg ccggagggag tgccggcggt agcgccggtg ggaagcttat ggtgagtaca   1080
ggggaggagc tgttcaccgg ggtggtgcca tttaaatttc aacttaaagg aaccatcaat   1140
ggcaaatcgt ttaccgttga aggcgaaggt gaaggaaatt cacatgaagg ttctcataaa   1200
ggaaaatatg tttgtacaag tggaaaacta ccgatgtcat gggcagcact tggaacatcc   1260
tttggttatg gaatgaaata ttataccaaa tatcctagtg gactgaagaa ctggtttcat   1320
gaagtaatgc ctgaaggctt tacctacgat cgtcatattc aatataaagg cgatgggagt   1380
atccatgcaa aacaccaaca ctttatgaaa aatgggactt atcacaacat tgttgaattt   1440
actggtcagg attttaaaga aaatagtcca gtcttaactg gagatatgaa tgtctcatta   1500
ccgaatgaag ttcaacatat acccagagat gatggagtag aatgcccagt gaccttgctt   1560
tatcctttat tatcggataa atcaaaatgc gttgaggctc accaaaatac aatctgcaag   1620
cctcttcata atcaaccagc acctgatgtc ccatatcact ggattcgtaa acaatacaca   1680
caaagcaaag atgataccga ggaacgtgat catatttgtc aatcagagac tctcgaagca   1740
cacttacctt ggcatgagcc ttcagcatcg gcagta                              1776


<210> SEQ ID NO 17
<211> LENGTH: 582
<212> TYPE: PRT
<213> ORGANISM: Cytaeis uchidae

<400> SEQUENCE: 17

Met Val Ser Thr Gly Glu Glu Leu Phe Thr Gly Val Val Pro Phe Lys
1               5                   10                  15

Phe Gln Leu Lys Gly Thr Ile Asn Gly Lys Ser Phe Thr Val Glu Gly
            20                  25                  30
```

```
Glu Gly Glu Gly Asn Ser His Glu Gly Ser His Lys Gly Lys Tyr Val
        35                  40                  45

Cys Thr Ser Gly Lys Leu Pro Met Ser Trp Ala Ala Leu Gly Thr Ser
    50                  55                  60

Phe Gly Tyr Gly Met Lys Tyr Tyr Thr Lys Tyr Pro Ser Gly Leu Lys
65                  70                  75                  80

Asn Trp Phe His Glu Val Met Pro Glu Gly Phe Thr Tyr Asp Arg His
                85                  90                  95

Ile Gln Tyr Lys Gly Asp Gly Ser Ile His Ala Lys His Gln His Phe
            100                 105                 110

Met Lys Asn Gly Thr Tyr His Asn Ile Val Glu Phe Thr Gly Gln Asp
        115                 120                 125

Phe Lys Glu Asn Ser Pro Val Leu Thr Gly Asp Met Asn Val Ser Leu
    130                 135                 140

Pro Asn Glu Val Gln His Ile Pro Arg Asp Asp Gly Val Glu Cys Pro
145                 150                 155                 160

Val Thr Leu Leu Tyr Pro Leu Leu Ser Asp Lys Ser Lys Cys Val Glu
                165                 170                 175

Ala Tyr Gln Asn Thr Ile Ile Lys Pro Leu His Asn Gln Pro Ala Pro
            180                 185                 190

Asp Val Pro Tyr His Trp Ile Arg Lys Gln Tyr Thr Gln Ser Lys Asp
        195                 200                 205

Asp Thr Glu Glu Arg Asp His Ile Ile Gln Ser Glu Thr Leu Glu Ala
    210                 215                 220

His Leu Pro Trp His Glu Pro Ser Ala Ser Ala Val Glu Phe Ser Ala
225                 230                 235                 240

Gly Gly Ser Ala Gly Gly Ser Ala Gly Gly Ser Ala Gly Gly Ser Ala
                245                 250                 255

Gly Gly Ser Gly Ser Ala Gly Gly Ser Ala Gly Gly Ser Thr Ser Ala
            260                 265                 270

Gly Gly Ser Ala Gly Gly Ser Ala Gly Gly Ser Ala Gly Gly Ser Ala
        275                 280                 285

Gly Gly Ser Gly Ser Ala Gly Gly Ser Ala Gly Gly Ser Thr Ser Ala
    290                 295                 300

Gly Gly Ser Ala Gly Gly Ser Ala Gly Gly Ser Ala Gly Gly Ser Ala
305                 310                 315                 320

Gly Gly Ser Gly Ser Ala Gly Gly Ser Ala Gly Gly Ser Thr Ser Ala
                325                 330                 335

Gly Gly Ser Ala Gly Gly Ser Ala Gly Gly Ser Ala Gly Gly Ser Ala
            340                 345                 350

Gly Gly Lys Leu Met Val Ser Thr Gly Glu Glu Leu Phe Thr Gly Val
        355                 360                 365

Val Pro Phe Lys Phe Gln Leu Lys Gly Thr Ile Asn Gly Lys Ser Phe
    370                 375                 380

Thr Val Glu Gly Glu Gly Glu Gly Asn Ser His Glu Gly Ser His Lys
385                 390                 395                 400

Gly Lys Tyr Val Cys Thr Ser Gly Lys Leu Pro Met Ser Trp Ala Ala
                405                 410                 415

Leu Gly Thr Ser Phe Gly Tyr Gly Met Lys Tyr Tyr Thr Lys Tyr Pro
            420                 425                 430

Ser Gly Leu Lys Asn Trp Phe His Glu Val Met Pro Glu Gly Phe Thr
        435                 440                 445
```

-continued

Tyr Asp Arg His Ile Gln Tyr Lys Gly Asp Gly Ser Ile His Ala Lys
    450                 455                 460

His Gln His Phe Met Lys Asn Gly Thr Tyr His Asn Ile Val Glu Phe
465                 470                 475                 480

Thr Gly Gln Asp Phe Lys Glu Asn Ser Pro Val Leu Thr Gly Asp Met
                485                 490                 495

Asn Val Ser Leu Pro Asn Glu Val Gln His Ile Pro Arg Asp Asp Gly
            500                 505                 510

Val Glu Cys Pro Val Thr Leu Leu Tyr Pro Leu Leu Ser Asp Lys Ser
        515                 520                 525

Lys Cys Val Glu Ala Tyr Gln Asn Thr Ile Ile Lys Pro Leu His Asn
    530                 535                 540

Gln Pro Ala Pro Asp Val Pro Tyr His Trp Ile Arg Lys Gln Tyr Thr
545                 550                 555                 560

Gln Ser Lys Asp Asp Thr Glu Glu Arg Asp His Ile Ile Gln Ser Glu
                565                 570                 575

Thr Leu Glu Ala His Leu
            580

<210> SEQ ID NO 18
<211> LENGTH: 1746
<212> TYPE: DNA
<213> ORGANISM: Cytaeis uchidae

<400> SEQUENCE: 18
atggtgtcta caggcgagga gctgtttacc ggcgtggtgc ccttcaagtt ccagctgaag 60
ggcaccatca acggcaagag cttcaccgtg gaaggcgagg gcgagggcaa tagccacgag 120
ggcagccaca aaggcaagta cgtgtgcacc agcggcaaac tgccaatgtc ttgggccgcc 180
ctgggaacta gcttcggcta tggcatgaag tactacacca agtaccccag cggcctgaag 240
aactggttcc acgaggtgat gcccgagggc ttcacctacg acagacacat ccagtacaag 300
ggcgacggca gcatccacgc caagcaccag cacttcatga agaacggcac ctaccacaac 360
atcgtggagt tcaccggcca ggacttcaag gagaacagcc ccgtgctgac cggcgacatg 420
aacgtgagcc tgcccaacga ggtgcagcac atccccagag atgacggcgt ggagtgccca 480
gtgaccctgc tgtaccctct gctgagcgac aagagcaagt gcgtggaggc ctaccagaac 540
accatcatca agcccctgca caatcagcca gcccccgatg tgccatacca ctggatcaga 600
aagcagtaca cccagagcaa ggacgacacc gaggagagag accacatcat ccagagcgag 660
accctggagg cccacctgcc atggcacgag ccttctgctt ctgccgtgga attcagtgct 720
ggtggttctg ctggaggaag cgccggaggt tccgctgggg gaagcgcagg cggctccggc 780
agcgctggcg ggagtgccgg gggcagtacc tccgcaggag gaagtgcagg gggaagcgct 840
ggtggcagtg cgggggggttc cgcaggcggt agcggttccg ccggtggatc tgccggtgga 900
agcacatctg ctgggggtag tgcaggaggg tccgctggtg ggagcgcagg tggatctgcc 960
ggggggtctg gaagtgcagg tggtagcgct ggagggtcca catctgcagg tgggtctgct 1020
ggcggttccg ccggagggag tgccggcggt agcgccggtg ggaagcttat ggtgagtaca 1080
ggggaggagc tgttcaccgg ggtggtgcca tttaaatttc aacttaaagg aaccatcaat 1140
ggcaaatcgt ttaccgttga aggcgaaggt gaaggaaatt cacatgaagg ttctcataaa 1200
ggaaaatatg tttgtacaag tggaaaacta ccgatgtcat gggcagcact tggaacatcc 1260
tttggttatg gaatgaaata ttataccaaa tatcctagtg gactgaagaa ctggtttcat 1320

```
gaagtaatgc ctgaaggctt tacctacgat cgtcatattc aatataaagg cgatgggagt   1380

atccatgcaa aacaccaaca ctttatgaaa aatgggactt atcacaacat tgttgaattt   1440

actggtcagg attttaaaga aaatagtcca gtcttaactg gagatatgaa tgtctcatta   1500

ccgaatgaag ttcaacatat acccagagat gatggagtag aatgcccagt gaccttgctt   1560

tatcctttat tatcggataa atcaaaatgc gttgaggctt accaaaatac aatcatcaag   1620

cctcttcata atcaaccagc acctgatgtc ccatatcact ggattcgtaa acaatacaca   1680

caaagcaaag atgataccga ggaacgtgat catattattc aatcagagac tctcgaagca   1740

cactta                                                              1746
```

```
<210> SEQ ID NO 19
<211> LENGTH: 485
<212> TYPE: PRT
<213> ORGANISM: Cytaeis uchidae

<400> SEQUENCE: 19

Met Val Ser Thr Gly Glu Glu Leu Phe Thr Gly Val Val Pro Phe Lys
1               5                   10                  15

Phe Gln Leu Lys Gly Thr Ile Asn Gly Lys Ser Phe Thr Val Glu Gly
            20                  25                  30

Glu Gly Glu Gly Asn Ser His Glu Gly Ser His Lys Gly Lys Tyr Val
        35                  40                  45

Cys Thr Ser Gly Lys Leu Pro Met Ser Trp Ala Ala Leu Gly Thr Ser
    50                  55                  60

Phe Gly Tyr Gly Met Lys Tyr Tyr Thr Lys Tyr Pro Ser Gly Leu Lys
65                  70                  75                  80

Asn Trp Phe His Glu Val Met Pro Glu Gly Phe Thr Tyr Asp Arg His
                85                  90                  95

Ile Gln Tyr Lys Gly Asp Gly Ser Ile His Ala Lys His Gln His Phe
            100                 105                 110

Met Lys Asn Gly Thr Tyr His Asn Ile Val Glu Phe Thr Gly Gln Asp
        115                 120                 125

Phe Lys Glu Asn Ser Pro Val Leu Thr Gly Asp Met Asn Val Ser Leu
    130                 135                 140

Pro Asn Glu Val Gln His Ile Pro Arg Asp Asp Gly Val Glu Cys Pro
145                 150                 155                 160

Val Thr Leu Leu Tyr Pro Leu Leu Ser Asp Lys Ser Lys Cys Val Glu
                165                 170                 175

Ala His Gln Asn Thr Ile Cys Lys Pro Leu His Asn Gln Pro Ala Pro
            180                 185                 190

Asp Val Pro Tyr His Trp Ile Arg Lys Gln Tyr Thr Gln Ser Lys Asp
        195                 200                 205

Asp Thr Glu Glu Arg Asp His Ile Cys Gln Ser Glu Thr Leu Glu Ala
    210                 215                 220

His Leu Pro Trp His Glu Pro Ser Ala Ser Ala Val Gly His Gly Thr
225                 230                 235                 240

Gly Ser Thr Gly Ser Gly Ser Ser Gly Thr Ala Ser Ser Glu Asp Asn
                245                 250                 255

Asn Ile Asp Met Val Ser Thr Gly Glu Glu Leu Phe Thr Gly Val Val
            260                 265                 270

Pro Phe Lys Phe Gln Leu Lys Gly Thr Ile Asn Gly Lys Ser Phe Thr
        275                 280                 285
```

```
Val Glu Gly Glu Gly Glu Gly Asn Ser His Glu Gly Ser His Lys Gly
    290                 295                 300

Lys Tyr Val Cys Thr Ser Gly Lys Leu Pro Met Ser Trp Ala Ala Leu
305                 310                 315                 320

Gly Thr Ser Phe Gly Tyr Gly Met Lys Tyr Tyr Thr Lys Tyr Pro Ser
                325                 330                 335

Gly Leu Lys Asn Trp Phe His Glu Val Met Pro Glu Gly Phe Thr Tyr
            340                 345                 350

Asp Arg His Ile Gln Tyr Lys Gly Asp Gly Ser Ile His Ala Lys His
        355                 360                 365

Gln His Phe Met Lys Asn Gly Thr Tyr His Asn Ile Val Glu Phe Thr
    370                 375                 380

Gly Gln Asp Phe Lys Glu Asn Ser Pro Val Leu Thr Gly Asp Met Asn
385                 390                 395                 400

Val Ser Leu Pro Asn Glu Val Gln His Ile Pro Arg Asp Asp Gly Val
                405                 410                 415

Glu Cys Pro Val Thr Leu Leu Tyr Pro Leu Leu Ser Asp Lys Ser Lys
            420                 425                 430

Cys Val Glu Ala His Gln Asn Thr Ile Cys Lys Pro Leu His Asn Gln
        435                 440                 445

Pro Ala Pro Asp Val Pro Tyr His Trp Ile Arg Lys Gln Tyr Thr Gln
    450                 455                 460

Ser Lys Asp Asp Thr Glu Glu Arg Asp His Ile Cys Gln Ser Glu Thr
465                 470                 475                 480

Leu Glu Ala His Leu
                485


<210> SEQ ID NO 20
<211> LENGTH: 1455
<212> TYPE: DNA
<213> ORGANISM: Cytaeis uchidae

<400> SEQUENCE: 20

atggtgtcta caggcgagga gctgtttacc ggcgtggtgc ccttcaagtt ccagctgaag      60

ggcaccatca acggcaagag cttcaccgtg gaaggcgagg gcgagggcaa tagccacgag     120

ggcagccaca aaggcaagta cgtgtgcacc agcggcaaac tgccaatgtc ttgggccgcc     180

ctgggaacta gcttcggcta tggcatgaag tactacacca agtaccccag cggcctgaag     240

aactggttcc acgaggtgat gcccgagggc ttcacctacg acagacacat ccagtacaag     300

ggcgacggca gcatccacgc caagcaccag cacttcatga agaacggcac ctaccacaac     360

atcgtggagt tcaccggcca ggacttcaag gagaacagcc ccgtgctgac cggcgacatg     420

aacgtgagcc tgcccaacga ggtgcagcac atccccagag atgacggcgt ggagtgccca     480

gtgaccctgc tgtaccctct gctgagcgac aagagcaagt gcgtggaggc ccaccagaac     540

accatctgca agcccctgca caatcagcca gcccccgatg tgccatacca ctggatcaga     600

aagcagtaca cccagagcaa ggacgacacc gaggagagag accacatctg ccagagcgag     660

accctggagg cccacctgcc atggcacgag ccttctgctt ctgccgtggg gcatggcacc     720

ggcagcaccg gcagcggcag ctccggcacc gcctcctccg aggacaacaa catcgatatg     780

gtgagtacag gggaggagct gttcaccggg gtggtgccat ttaaatttca acttaaagga     840

accatcaatg gcaaatcgtt taccgttgaa ggcgaaggtg aaggaaattc acatgaaggt     900

tctcataaag gaaaatatgt ttgtacaagt ggaaaactac cgatgtcatg ggcagcactt     960
```

```
ggaacatcct ttggttatgg aatgaaatat tataccaaat atcctagtgg actgaagaac   1020

tggtttcatg aagtaatgcc tgaaggcttt acctacgatc gtcatattca atataaaggc   1080

gatgggagta tccatgcaaa acaccaacac tttatgaaaa atgggactta tcacaacatt   1140

gttgaattta ctggtcagga ttttaaagaa aatagtccag tcttaactgg agatatgaat   1200

gtctcattac cgaatgaagt tcaacatata cccagagatg atggagtaga atgcccagtg   1260

accttgcttt atcctttatt atcggataaa tcaaaatgcg ttgaggctca ccaaaataca   1320

atctgcaagc ctcttcataa tcaaccagca cctgatgtcc catatcactg gattcgtaaa   1380

caatacacac aaagcaaaga tgataccgag gaacgtgatc atatttgtca atcagagact   1440

ctcgaagcac actta                                                    1455


<210> SEQ ID NO 21
<211> LENGTH: 258
<212> TYPE: PRT
<213> ORGANISM: Cytaeis uchidae

<400> SEQUENCE: 21

Met Leu Leu Pro Val Pro Leu Leu Leu Gly Leu Leu Gly Ala Ala Ala
1               5                   10                  15

Asp Pro Met Val Ser Lys Gly Glu Glu Leu Phe Thr Gly Val Thr Pro
            20                  25                  30

Phe Lys Phe Gln Leu Lys Gly Thr Ile Asn Gly Lys Ser Phe Thr Val
        35                  40                  45

Glu Gly Glu Gly Glu Gly Asn Ser His Glu Gly Ser His Lys Gly Lys
    50                  55                  60

Tyr Val Cys Thr Ser Gly Lys Leu Pro Met Ser Trp Ala Ala Leu Gly
65                  70                  75                  80

Thr Ser Phe Gly Tyr Gly Met Lys Tyr Tyr Thr Lys Tyr Pro Ser Gly
                85                  90                  95

Leu Lys Asn Trp Phe His Glu Val Met Pro Glu Gly Phe Thr Tyr Asp
            100                 105                 110

Arg His Ile Gln Tyr Lys Gly Asp Gly Ser Ile His Ala Lys His Gln
        115                 120                 125

His Phe Met Lys Asn Gly Thr Tyr His Asn Ile Val Glu Phe Thr Gly
    130                 135                 140

Gln Asp Phe Lys Glu Asn Ser Pro Val Leu Thr Gly Asp Met Asn Val
145                 150                 155                 160

Ser Leu Pro Asn Glu Val Gln His Ile Pro Arg Asp Asp Gly Val Glu
                165                 170                 175

Cys Pro Val Thr Leu Leu Tyr Pro Leu Leu Ser Asp Lys Ser Lys Cys
            180                 185                 190

Val Glu Ala Tyr Gln Asn Thr Ile Ile Lys Pro Leu His Asn Gln Pro
        195                 200                 205

Ala Pro Asp Val Pro Tyr His Trp Ile Arg Lys Gln Tyr Thr Gln Ser
    210                 215                 220

Lys Asp Asp Thr Glu Glu Arg Asp His Ile Ile Gln Ser Glu Thr Leu
225                 230                 235                 240

Glu Ala His Leu Pro Trp His Glu Pro Ser Ala Ser Ala Val Lys Asp
                245                 250                 255

Glu Leu


<210> SEQ ID NO 22
<211> LENGTH: 774
```

<212> TYPE: DNA
<213> ORGANISM: Cytaeis uchidae

<400> SEQUENCE: 22
atgctgctgc ccgtccccct gctgctgggc ctgctgggcg ccgccgcgga tccgatggtg 60
agcaagggcg aggagctgtt tacaggcgtg accccccttca agttccagct gaagggcacc 120
atcaacggca agagcttcac cgtggaaggc gagggcgagg gcaatagcca cgagggcagc 180
cacaaaggca agtacgtgtg caccagcggc aaactgccaa tgtcttgggc cgccctggga 240
actagcttcg gctatggcat gaagtactac accaagtacc ccagcggcct gaagaactgg 300
ttccacgagg tgatgcccga gggcttcacc tacgacagac acatccagta caagggcgac 360
ggcagcatcc acgccaagca ccagcacttc atgaagaacg gcacctacca caacatcgtg 420
gagttcaccg gccaggactt caaggagaac agccccgtgc tgaccggcga catgaacgtg 480
agcctgccca acgaggtgca gcacatcccc agagatgacg gcgtggagtg cccagtgacc 540
ctgctgtacc ctctgctgag cgacaagagc aagtgcgtgg aggcctacca gaacaccatc 600
atcaagcccc tgcacaatca gccagccccc gatgtgccat accactggat cagaaagcag 660
tacacccaga gcaaggacga caccgaggag agagaccaca tcatccagag cgagaccctg 720
gaggcccacc tgccatggca cgagccttct gcttctgccg tgaaggatga actg 774

<210> SEQ ID NO 23
<211> LENGTH: 291
<212> TYPE: PRT
<213> ORGANISM: Cytaeis uchidae

<400> SEQUENCE: 23

Met Ser Val Leu Thr Pro Leu Leu Leu Arg Gly Leu Thr Gly Ser Ala
1               5                   10                  15

Arg Arg Leu Pro Val Pro Arg Ala Lys Ile His Ser Leu Pro Pro Glu
            20                  25                  30

Gly Lys Leu Gly Met Ser Val Leu Thr Pro Leu Leu Leu Arg Gly Leu
        35                  40                  45

Thr Gly Ser Ala Arg Arg Leu Pro Val Pro Arg Ala Lys Ile His Ser
    50                  55                  60

Leu Pro Pro Glu Gly Lys Leu Gly Gly Ser Met Ala Ser Thr Pro Phe
65                  70                  75                  80

Lys Phe Gln Leu Lys Gly Thr Ile Asn Gly Lys Ser Phe Thr Val Glu
                85                  90                  95

Gly Glu Gly Glu Gly Asn Ser His Glu Gly Ser His Lys Gly Lys Tyr
            100                 105                 110

Val Cys Thr Ser Gly Lys Leu Pro Met Ser Trp Ala Ala Leu Gly Thr
        115                 120                 125

Ser Phe Gly Tyr Gly Met Lys Tyr Tyr Thr Lys Tyr Pro Ser Gly Leu
    130                 135                 140

Lys Asn Trp Phe His Glu Val Met Pro Glu Gly Phe Thr Tyr Asp Arg
145                 150                 155                 160

His Ile Gln Tyr Lys Gly Asp Gly Ser Ile His Ala Lys His Gln His
                165                 170                 175

Phe Met Lys Asn Gly Thr Tyr His Asn Ile Val Glu Phe Thr Gly Gln
            180                 185                 190

Asp Phe Lys Glu Asn Ser Pro Val Leu Thr Gly Asp Met Asn Val Ser
        195                 200                 205

Leu Pro Asn Glu Val Gln His Ile Pro Arg Asp Asp Gly Val Glu Cys
210 215 220

Pro Val Thr Leu Leu Tyr Pro Leu Leu Ser Asp Lys Ser Lys Cys Val
225 230 235 240

Glu Ala His Gln Asn Thr Ile Cys Lys Pro Leu His Asn Gln Pro Ala
245 250 255

Pro Asp Val Pro Tyr His Trp Ile Arg Lys Gln Tyr Thr Gln Ser Lys
260 265 270

Asp Asp Thr Glu Glu Arg Asp His Ile Cys Gln Ser Glu Thr Leu Glu
275 280 285

Ala His Leu
290

<210> SEQ ID NO 24
<211> LENGTH: 876
<212> TYPE: DNA
<213> ORGANISM: Cytaeis uchidae

<400> SEQUENCE: 24
atgtccgtcc tgacgccgct gctgctgcgg ggcttgacag gctcggcccg gcggctccca 60
gtgccgcgcg ccaagatcca ttcgttgccg ccggaggga agcttgggat gtccgtcctg 120
acgccgctgc tgctgcgggg cttgacaggc tcggcccggc ggctcccagt gccgcgcgcc 180
aagatccatt cgttgccgcc ggaggggaag ctcgggggat ccatggccag cacccccttc 240
aagttccagc tgaagggcac catcaacggc aagagcttca ccgtggaagg cgagggcgag 300
ggcaatagcc acgagggcag ccacaaaggc aagtacgtgt gcaccagcgg caaactgcca 360
atgtcttggg ccgccctggg aactagcttc ggctatggca tgaagtacta caccaagtac 420
cccagcggcc tgaagaactg gttccacgag gtgatgcccg agggcttcac ctacgacaga 480
cacatccagt acaagggcga cggcagcatc cacgccaagc accagcactt catgaagaac 540
ggcacctacc acaacatcgt ggagttcacc ggccaggact tcaaggagaa cagccccgtg 600
ctgaccggcg acatgaacgt gagcctgccc aacgaggtgc agcacatccc cagagatgac 660
ggcgtggagt gcccagtgac cctgctgtac cctctgctga gcgacaagag caagtgcgtg 720
gaggcccacc agaacaccat ctgcaagccc ctgcacaatc agccagcccc cgatgtgcca 780
taccactgga tcagaaagca gtacacccag agcaaggacg acaccgagga gagagaccac 840
atctgccaga gcgagaccct ggaggcccac ctgtaa 876

<210> SEQ ID NO 25
<211> LENGTH: 300
<212> TYPE: PRT
<213> ORGANISM: Cytaeis uchidae

<400> SEQUENCE: 25

Met Ser Val Leu Thr Pro Leu Leu Leu Arg Gly Leu Thr Gly Ser Ala
1 5 10 15

Arg Arg Leu Pro Val Pro Arg Ala Lys Ile His Ser Leu Pro Pro Glu
20 25 30

Gly Lys Leu Gly Met Ser Val Leu Thr Pro Leu Leu Leu Arg Gly Leu
35 40 45

Thr Gly Ser Ala Arg Arg Leu Pro Val Pro Arg Ala Lys Ile His Ser
50 55 60

Leu Pro Pro Glu Gly Lys Leu Gly Gly Ser Met Ala Ser Thr Gly Glu
65 70 75 80

```
Glu Leu Phe Thr Gly Val Val Pro Phe Lys Phe Gln Leu Lys Gly Thr
                85                  90                  95

Ile Asn Gly Lys Ser Phe Thr Val Glu Gly Glu Gly Glu Gly Asn Ser
            100                 105                 110

His Glu Gly Ser His Lys Gly Lys Tyr Val Cys Thr Ser Gly Lys Leu
        115                 120                 125

Pro Met Ser Trp Ala Ala Leu Gly Thr Ser Phe Gly Tyr Gly Met Lys
    130                 135                 140

Tyr Tyr Thr Lys Tyr Pro Ser Gly Leu Lys Asn Trp Phe His Glu Val
145                 150                 155                 160

Met Pro Glu Gly Phe Thr Tyr Asp Arg His Ile Gln Tyr Lys Gly Asp
                165                 170                 175

Gly Ser Ile His Ala Lys His Gln His Phe Met Lys Asn Gly Thr Tyr
            180                 185                 190

His Asn Ile Val Glu Phe Thr Gly Gln Asp Phe Lys Glu Asn Ser Pro
        195                 200                 205

Val Leu Thr Gly Asp Met Asn Val Ser Leu Pro Asn Glu Val Gln His
    210                 215                 220

Ile Pro Arg Asp Asp Gly Val Glu Cys Pro Val Thr Leu Leu Tyr Pro
225                 230                 235                 240

Leu Leu Ser Asp Lys Ser Lys Cys Val Glu Ala His Gln Asn Thr Ile
                245                 250                 255

Cys Lys Pro Leu His Asn Gln Pro Ala Pro Asp Val Pro Tyr His Trp
            260                 265                 270

Ile Arg Lys Gln Tyr Thr Gln Ser Lys Asp Asp Thr Glu Glu Arg Asp
        275                 280                 285

His Ile Cys Gln Ser Glu Thr Leu Glu Ala His Leu
    290                 295                 300
```

<210> SEQ ID NO 26
<211> LENGTH: 903
<212> TYPE: DNA
<213> ORGANISM: Cytaeis uchidae

<400> SEQUENCE: 26

```
atgtccgtcc tgacgccgct gctgctgcgg ggcttgacag gctcggcccg gcggctccca      60

gtgccgcgcg ccaagatcca ttcgttgccg ccggaggga agcttgggat gtccgtcctg      120

acgccgctgc tgctgcgggg cttgacaggc tcggcccggc ggctcccagt gccgcgcgcc     180

aagatccatt cgttgccgcc ggaggggaag ctcgggggat ccatggccag caccggggag     240

gagctgttca ccggggtggt gcccttcaag ttccagctga agggcaccat caacggcaag     300

agcttcaccg tggaaggcga gggcgagggc aatagccacg agggcagcca caaaggcaag     360

tacgtgtgca ccagcggcaa actgccaatg tcttgggccg ccctgggaac tagcttcggc     420

tatggcatga agtactacac caagtacccc agcggcctga agaactggtt ccacgaggtg     480

atgcccgagg gcttcaccta cgacagacac atccagtaca agggcgacgg cagcatccac     540

gccaagcacc agcacttcat gaagaacggc acctaccaca acatcgtgga gttcaccggc     600

caggacttca aggagaacag ccccgtgctg accggcgaca tgaacgtgag cctgcccaac     660

gaggtgcagc acatccccag agatgacggc gtggagtgcc cagtgaccct gctgtaccct     720

ctgctgagcg acaagagcaa gtgcgtggag gcccaccaga acaccatctg caagcccctg     780
```

cacaatcagc cagccccga tgtgccatac cactggatca gaaagcagta cacccagagc 840
aaggacgaca ccgaggagag agaccacatc tgccagagcg agaccctgga ggcccacctg 900
taa 903

<210> SEQ ID NO 27
<211> LENGTH: 217
<212> TYPE: PRT
<213> ORGANISM: Cytaeis uchidae

<400> SEQUENCE: 27

Met Ala Ser Thr Pro Phe Lys Phe Gln Leu Lys Gly Thr Ile Asn Gly
1 5 10 15

Lys Ser Phe Thr Val Glu Gly Glu Gly Glu Gly Asn Ser His Glu Gly
20 25 30

Ser His Lys Gly Lys Tyr Val Cys Thr Ser Gly Lys Leu Pro Met Ser
35 40 45

Trp Ala Ala Leu Gly Thr Ser Phe Gly Tyr Gly Met Lys Tyr Tyr Thr
50 55 60

Lys Tyr Pro Ser Gly Leu Lys Asn Trp Phe His Glu Val Met Pro Glu
65 70 75 80

Gly Phe Thr Tyr Asp Arg His Ile Gln Tyr Lys Gly Asp Gly Ser Ile
85 90 95

His Ala Lys His Gln His Phe Met Lys Asn Gly Thr Tyr His Asn Ile
100 105 110

Val Glu Phe Thr Gly Gln Asp Phe Lys Glu Asn Ser Pro Val Leu Thr
115 120 125

Gly Asp Met Asn Val Ser Leu Pro Asn Glu Val Gln His Ile Pro Arg
130 135 140

Asp Asp Gly Val Glu Cys Pro Val Thr Leu Leu Tyr Pro Leu Leu Ser
145 150 155 160

Asp Lys Ser Lys Cys Val Glu Ala His Gln Asn Thr Ile Cys Lys Pro
165 170 175

Leu His Asn Gln Pro Ala Pro Asp Val Pro Ala His Trp Ile Arg Lys
180 185 190

Gln Tyr Thr Gln Ser Lys Asp Asp Thr Glu Glu Arg Asp His Ile Cys
195 200 205

Gln Ser Glu Thr Leu Glu Ala His Leu
210 215

<210> SEQ ID NO 28
<211> LENGTH: 651
<212> TYPE: DNA
<213> ORGANISM: Cytaeis uchidae

<400> SEQUENCE: 28
atggcctcta caccccttcaa gttccagctg aagggcacca tcaacggcaa gagcttcacc 60
gtggaaggcg agggcgaggg caatagccac gagggcagcc acaaaggcaa gtacgtgtgc 120
accagcggca aactgccaat gtcttgggcc gccctgggaa ctagcttcgg ctatggcatg 180
aagtactaca ccaagtaccc cagcggcctg aagaactggt tccacgaggt gatgcccgag 240
ggcttcacct acgacagaca catccagtac aagggcgacg gcagcatcca cgccaagcac 300
cagcacttca tgaagaacgg cacctaccac aacatcgtgg agttcaccgg ccaggacttc 360
aaggagaaca gccccgtgct gaccggcgac atgaacgtga gcctgcccaa cgaggtgcag 420

```
cacatcccca gagatgacgg cgtggagtgc ccagtgaccc tgctgtaccc tctgctgagc    480

gacaagagca agtgcgtgga ggcccaccag aacaccatct gcaagcccct gcacaatcag    540

ccagcccccg atgtgccagc ccactggatc agaaagcagt acacccagag caaggacgac    600

accgaggaga gagaccacat ctgccagagc gagaccctgg aggcccacct g             651


<210> SEQ ID NO 29
<211> LENGTH: 217
<212> TYPE: PRT
<213> ORGANISM: Cytaeis uchidae

<400> SEQUENCE: 29

Met Ala Ser Thr Pro Phe Lys Phe Gln Leu Lys Gly Thr Ile Asn Gly
1               5                   10                  15

Lys Ser Phe Thr Val Glu Gly Glu Gly Glu Gly Asn Ser His Glu Gly
            20                  25                  30

Ser His Lys Gly Lys Tyr Val Cys Thr Ser Gly Lys Leu Pro Met Ser
        35                  40                  45

Trp Ala Ala Leu Gly Thr Ser Phe Gly Tyr Gly Met Lys Tyr Tyr Thr
    50                  55                  60

Lys Tyr Pro Ser Gly Leu Lys Asn Trp Phe His Glu Val Met Pro Glu
65                  70                  75                  80

Gly Phe Thr Tyr Asp Arg His Ile Gln Tyr Lys Gly Asp Gly Ser Ile
                85                  90                  95

His Ala Lys His Gln His Phe Met Lys Asn Gly Thr Tyr His Asn Ile
            100                 105                 110

Val Glu Phe Thr Gly Gln Asp Phe Lys Glu Asn Ser Pro Val Leu Thr
        115                 120                 125

Gly Asp Met Asn Val Ser Leu Pro Asn Glu Val Gln His Ile Pro Arg
    130                 135                 140

Asp Asp Gly Val Glu Cys Pro Val Thr Leu Thr Tyr Pro Leu Leu Ser
145                 150                 155                 160

Asp Lys Ser Lys Cys Val Glu Ala His Gln Asn Thr Ile Cys Lys Pro
                165                 170                 175

Leu His Asn Gln Pro Ala Pro Asp Val Pro Tyr His Trp Ile Arg Lys
            180                 185                 190

Gln Tyr Thr Gln Ser Lys Asp Asp Thr Glu Glu Arg Asp His Ile Cys
        195                 200                 205

Gln Ser Glu Thr Leu Glu Ala His Leu
    210                 215


<210> SEQ ID NO 30
<211> LENGTH: 651
<212> TYPE: DNA
<213> ORGANISM: Cytaeis uchidae

<400> SEQUENCE: 30

atggcctcta cacccttcaa gttccagctg aagggcacca tcaacggcaa gagcttcacc     60

gtggaaggcg agggcgaggg caatagccac gagggcagcc acaaaggcaa gtacgtgtgc    120

accagcggca aactgccaat gtcttgggcc gccctgggaa ctagcttcgg ctatggcatg    180

aagtactaca ccaagtaccc cagcggcctg aagaactggt tccacgaggt gatgcccgag    240

ggcttcacct acgacagaca catccagtac aagggcgacg gcagcatcca cgccaagcac    300

cagcacttca tgaagaacgg cacctaccac aacatcgtgg agttcaccgg ccaggacttc    360

aaggagaaca gccccgtgct gaccggcgac atgaacgtga gcctgcccaa cgaggtgcag    420
```

```
cacatcccca gagatgacgg cgtggagtgc ccagtgaccc tgacgtaccc tctgctgagc    480

gacaagagca agtgcgtgga ggcccaccag aacaccatct gcaagcccct gcacaatcag    540

ccagcccccg atgtgccata ccactggatc agaaagcagt acacccagag caaggacgac    600

accgaggaga gagaccacat ctgccagagc gagaccctgg aggcccacct g             651


<210> SEQ ID NO 31
<211> LENGTH: 226
<212> TYPE: PRT
<213> ORGANISM: Cytaeis uchidae

<400> SEQUENCE: 31

Met Val Ser Thr Gly Glu Glu Leu Phe Thr Gly Val Val Pro Phe Lys
1               5                   10                  15

Phe Gln Leu Lys Gly Thr Ile Asn Gly Lys Ser Phe Thr Val Glu Gly
            20                  25                  30

Glu Gly Glu Gly Asn Ser His Glu Gly Ser His Lys Gly Lys Tyr Val
        35                  40                  45

Cys Thr Ser Gly Lys Leu Pro Met Ser Trp Ala Ala Leu Gly Thr Ser
    50                  55                  60

Phe Gly Tyr Gly Met Lys Tyr Tyr Thr Lys Tyr Pro Ser Gly Leu Lys
65                  70                  75                  80

Asn Trp Phe His Glu Val Met Pro Glu Gly Phe Thr Tyr Asp Arg His
                85                  90                  95

Ile Gln Tyr Lys Gly Asp Gly Ser Ile His Ala Lys His Gln His Phe
            100                 105                 110

Met Lys Asn Gly Thr Tyr His Asn Ile Val Glu Phe Thr Gly Gln Asp
        115                 120                 125

Phe Lys Glu Asn Ser Pro Val Leu Thr Gly Asp Met Asn Val Ser Leu
    130                 135                 140

Pro Asn Glu Val Gln His Ile Pro Arg Asp Asp Gly Val Glu Cys Pro
145                 150                 155                 160

Val Thr Leu Thr Tyr Pro Leu Leu Ser Asp Lys Ser Lys Cys Val Glu
                165                 170                 175

Ala Tyr Gln Asn Thr Ile Ile Lys Pro Leu His Asn Gln Pro Ala Pro
            180                 185                 190

Asp Val Pro Tyr His Trp Ile Arg Lys Gln Tyr Thr Gln Ser Lys Asp
        195                 200                 205

Asp Thr Glu Glu Arg Asp His Ile Ile Gln Ser Glu Thr Leu Glu Ala
    210                 215                 220

His Leu
225


<210> SEQ ID NO 32
<211> LENGTH: 678
<212> TYPE: DNA
<213> ORGANISM: Cytaeis uchidae

<400> SEQUENCE: 32

atggtgtcta caggcgagga gctgtttacc ggcgtggtgc ccttcaagtt ccagctgaag     60

ggcaccatca acggcaagag cttcaccgtg gaaggcgagg gcgagggcaa tagccacgag    120

ggcagccaca aaggcaagta cgtgtgcacc agcggcaaac tgccaatgtc ttgggccgcc    180

ctgggaacta gcttcggcta tggcatgaag tactacacca agtaccccag cggcctgaag    240

aactggttcc acgaggtgat gcccgagggc ttcacctacg acagacacat ccagtacaag    300
```

```
ggcgacggca gcatccacgc caagcaccag cacttcatga agaacggcac ctaccacaac    360

atcgtggagt tcaccggcca ggacttcaag gagaacagcc ccgtgctgac cggcgacatg    420

aacgtgagcc tgcccaacga ggtgcagcac atccccagag atgacggcgt ggagtgccca    480

gtgaccctga cgtaccctct gctgagcgac aagagcaagt gcgtggaggc ctaccagaac    540

accatcatca agcccctgca caatcagcca gcccccgatg tgccatacca ctggatcaga    600

aagcagtaca cccagagcaa ggacgacacc gaggagagag accacatcat ccagagcgag    660

accctggagg cccacctg                                                  678


<210> SEQ ID NO 33
<211> LENGTH: 239
<212> TYPE: PRT
<213> ORGANISM: Artificial Sequence
<220> FEATURE:
<223> OTHER INFORMATION: Synthetic Sequence

<400> SEQUENCE: 33

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

POLYPEPTIDE EXHIBITING FLUORESCENT PROPERTIES AND USE FOR SAME

SEQUENCE LISTING

The text of the computer readable sequence listing filed herewith, titled "HARAK_42361_251_Corrected_SequenceListing", created Jun. 4, 2026, having a file size of 61,235 bytes, is hereby incorporated by reference in its entirety.

TECHNICAL FIELD

The present invention relates to a novel polypeptide which exhibit a fluorescence property, and uses of the polypeptide.

BACKGROUND ART

Fluorescent proteins have become an indispensable tool for visualizing a cell, tissue, an individual organism, or the like.

In recent years, the development of various kinds of bio-imaging technology in which fluorescent proteins are used has been in progress, and mutants of various publicly known fluorescent proteins have been reported (Non-Patent Literatures 1 to 5).

CITATION LIST

Non-Patent Literature

[Non-Patent Literature 1]
Shaner, N. C. et al., Nature Methods 5, 545-551, 2008
[Non-Patent Literature 2]
Shaner, N. C., Methods in Cell Biology 123, 95-111, 2014
[Non-Patent Literature 3]
Bindels, D. S. et al. Nature Methods 14, 53-56, 2017
[Non-Patent Literature 4]
Zhong, S. et al. Journal of Neuroscience Methods 313, 68-76, 2019
[Non-Patent Literature 5]
Shaner, N.C. et al. Nature Methods 10, 407-409, 2013

SUMMARY OF INVENTION

Technical Problem

Photostability of a fluorochrome is one of the urgent issues in the bio-imaging technology. Occurrence of fading makes it difficult to observe, over a sufficiently long time, fluorescence signals from a small copy number of molecules under observation. In particular, in a single-molecule imaging or in imaging with a limited amount of introduced fluorochromes, fading is a critical issue. In addition, occurrence of fading also makes it difficult to quantitatively evaluate a phenomena under observation. In this context, there is a demand for the development of a fluorescent protein more excellent in photostability than previously-reported fluorescent proteins.

The present inventors have successfully isolated a novel green fluorescent protein from *Cytaeis uchidae.*

An object of the present invention is to provide a novel fluorescent protein which exhibits useful properties, and uses of the fluorescent protein.

Solution to Problem

In order for the above problems to be solved, the present invention encompass any one of the following aspects.

<1> A polypeptide having a fluorescence property indicated in any one of (1) to (3) below:

(1) a polypeptide having an amino acid sequence set forth in SEQ ID NO: 1;

(2) a polypeptide having an amino acid sequence set forth in SEQ ID NO: 1, the amino acid sequence having replaced, deleted, inserted, and/or added therein not less than 1 and not more than 32 amino acids; and (3) a polypeptide having not less than 85% sequence identity with respect to an amino acid sequence set forth in SEQ ID NO: 1.

<2> The polypeptide described in <1>, in which the polypeptide exhibits higher photostability than EGFP or has brighter fluorescence than EGFP.

<3> The polypeptide described in <1> or <2>, in which the polypeptide has an amino acid sequence in which amino acid 168 of an amino acid sequence set forth in SEQ ID NO: 1 is alanine and which exhibits not less than 85% sequence identity with respect to an amino acid sequence set forth in SEQ ID NO: 1.

<4> A polynucleotide indicated in any one of (1) to (3) below:

(1) a polynucleotide which encodes a polypeptide having an amino acid sequence set forth in SEQ ID NO: 1;

(2) a polynucleotide which encodes a polypeptide having an amino acid sequence set forth in SEQ ID NO: 1, the amino acid sequence having replaced, deleted, inserted, and/or added therein not less than 1 and not more than 32 amino acids, the polypeptide having a fluorescence property; and (3) a polynucleotide which encodes a polypeptide having not less than 85% sequence identity with respect to an amino acid sequence set forth in SEQ ID NO: 1 and having a fluorescence property.

<5> An expression cassette including: (a) an expression regulatory region functional in an expression host; and (b) the polynucleotide described in <4>.

<6> A vector including: the polynucleotide described in <4> or the expression cassette described in <5>.

<7> A transformant including: the polynucleotide described in <4>, the expression cassette described in <5>, or the vector described in <6>.

<8> The transformant described in <7>, in which the transformant is a non-human transgenic organism.

<9> A fusion polypeptide including: the polypeptide described in any one of <1> to <3>; and another polypeptide.

<10> The fusion polypeptide described in <9>, in which the fusion polypeptide includes not less than two polypeptides linked together each of which is the polypeptide described in any one of <1> to <3>.

<11> A kit including the polypeptide described in any one of <1> to <3>, the polynucleotide described in <4>, the expression cassette described in <5>, the vector described in <6>, the transformant described in <7> or <8>, or the fusion polypeptide described in <9> or <10>.

<12> A method for observing fluorescence including: a producing step of producing, in a cell, the polypeptide described in any one of <1> to <3> or the fusion polypeptide described in <9> or <10>; an excitation light irradiating step of irradiating the cell with excitation light; and an observing step of observing fluorescence originating from the polypeptide or the fusion polypeptide.

Advantageous Effects of Invention

The present invention provides a fluorescent polypeptide having extremely high photostability. The fluorescent polypeptide of the present invention is advantageously useful in many fields including the field of molecular biology.

BRIEF DESCRIPTION OF DRAWINGS

FIG. 4 is an alignment of the amino acid sequences of StayGold(SEQ ID NO:1), CU17S(SEQ ID NO:4), and EGFP(SEQ ID NO:33) proteins of the present invention.

FIG. 5 is a diagram illustrating a simple comparison of a change in fluorescence intensity over time among five kinds of green fluorescent proteins, for the case of using purified proteins, in accordance with Examples of the present invention.

DESCRIPTION OF EMBODIMENTS

Figure 1:
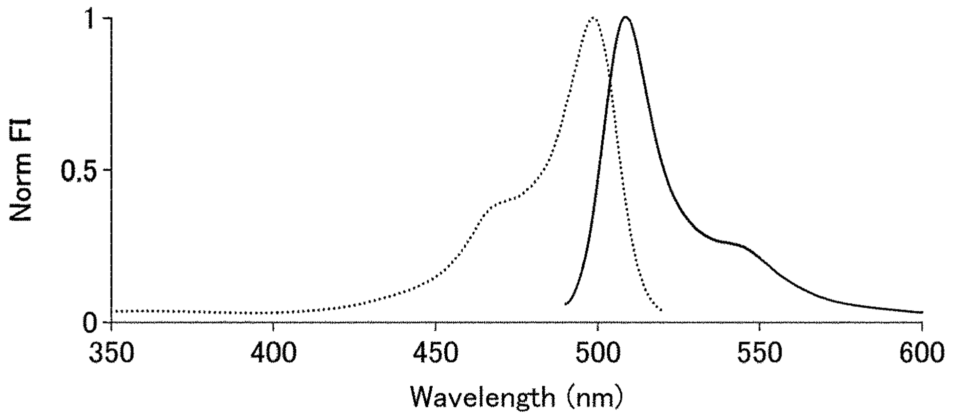
FIG. 1 is a diagram illustrating a fluorescence excitation spectrum and a fluorescence emission spectrum observed in *C. uchidae* in accordance with Examples of the present invention.

Definitions of Terms, Etc.

As used herein, a "polynucleotide" is interchangeable with a "nucleic acid" or a "nucleic acid molecule". The "polynucleotide" encompasses a polynucleotide that contains a known analog of a naturally occurring nucleotide, the analog being capable of functioning in the same manner as a naturally occurring nucleotide, unless otherwise set forth herein. A "base sequence" is interchangeable with a "nucleic acid sequence" or a "nucleotide sequence". A "base sequence" is intended to mean a deoxyribonucleotide sequence or a ribonucleotide sequence, unless otherwise noted. The polynucleotide may be single-stranded, or may be double-stranded. In the case of being single-stranded, the polynucleotide may be a sense strand or an antisense strand.

As used herein, a "gene" refers to the "polynucleotide" that encodes a protein.

As used herein, an "expression regulatory region" of a gene refers to the "polynucleotide" that regulates the expression of the gene. Examples of the "expression regulatory region" encompass a promoter region and an enhancer region.

As used herein, an "expression cassette" refers to an expression unit that includes: the expression regulatory region functional in an expression host; and the polynucleotide operably linked to the expression regulatory region. In the expression cassette, the polynucleotide is preferably a gene or a gene fragment. An example of the expression cassette has the above expression regulatory region and the above polynucleotide linked together in a genetically engineered manner therein. The phrase "operably linked" refers to a state in which expression of a polynucleotide is controlled by an expression regulatory sequence. The expression cassette may be in the form of an expression vector.

As used herein, a "polypeptide" is interchangeable with a "protein". The "polypeptide" includes a structure of amino acids linked together via peptide bonds. The "polypeptide" may further include a structure such as, for example, a sugar chain or an isoprenoid group. The "polypeptide" encompasses a polypeptide that contains a known analog of a naturally occurring amino acid, the analog being capable of functioning in the same manner as a naturally occurring amino acid, unless otherwise set forth herein.

As used herein, a "fluorescent polypeptide" refers to the polypeptide having a fluorescence property. The polypeptide having a fluorescence property refers to the polypeptide having a property of emitting fluorescence due to reception of irradiation of excitation light with a predetermined wavelength.

As used herein, the phrase "A and/or B" is a concept that encompasses both "A and B" and "A or B", and is interchangeable with the phase "at least one selected from the group consisting of A and B".

[1. Polypeptide Having Fluorescence Property]

A polypeptide of the present invention is a polypeptide (fluorescent polypeptide) having a fluorescence property, the polypeptide being indicated in the following (1) to (3).

(1) A polypeptide having an amino acid sequence set forth in SEQ ID NO: 1;

(2) a polypeptide having an amino acid sequence set forth in SEQ ID NO: 1, the amino acid sequence having replaced, deleted, inserted, and/or added therein not less than 1 and not more than 32 amino acids. Note that the number of amino acids having been replaced, deleted, inserted and/or added is preferably not less than 1 and not more than 26, more preferably not less than 1 and not more than 21, more preferably not less than 1 and not more than 10, more preferably not less than 1 and not more than 8, even more preferably not less than 1 and not more than 6, and particularly preferably not less than 1 and not more than 4. Hereinafter, the replacement, deletion, insertion, and/or addition of an amino acid are collectively referred to as a mutation of an amino acid.

(3) A polypeptide having not less than 85% sequence identity with respect to an amino acid sequence set forth in SEQ ID NO: 1. Note that the sequence identity is preferably not less than 88%, more preferably not less than 90%, more preferably not less than 95%, more preferably not less than 96%, even more preferably not less than 97%, and particularly preferably not less than 98% or not less than 99%.

The origin of the fluorescent polypeptide is not limited, but may be, for example, a chemically-synthesized fluorescent polypeptide, or may be a fluorescent polypeptide produced with use of genetic recombination technology. More specifically, an isolated and purified polypeptide, a chemically-synthesized polypeptide, and a polypeptide produced from a host cell on the basis of genetic recombination technology are within the scope of the fluorescent polypeptide. The host cell will be described in detail in the section "Transformant".

Examples of the fluorescent polypeptide of the present invention encompass a fluorescent polypeptide derived from *Cytaeis uchidae*. The present inventors have successfully isolated a novel green fluorescent protein from *Cytaeis uchidae*. Further, by modifying the novel fluorescent protein, the present inventors have successfully obtained a mutant which is bright and the fluorescence of which does not fade for a long time. An example of the fluorescent polypeptide is a fluorescent polypeptide having an amino acid sequence set forth in SEQ ID NO: 1, and is referred to as "StayGold". StayGold has bright fluorescence, and has photostability which is significantly higher than any other previously publicly known fluorescent proteins that are currently available.

The main fluorescence characteristics of StayGold are as follows:

Maximum excitation wavelength (nm): 496

Maximum fluorescence wavelength (nm): 505 (green)

Molar extinction coefficient ($M^{-1}$ $cm^{-1}$): 159000 (for 496 nm)

Quantum yield (%): 93

Fluorescence lifetime (nanoseconds): 2.81

The fluorescent polypeptide indicated in the above (2) or (3) can be considered a mutant with the fluorescent polypeptide indicated in the above (1) as reference. The fluorescent polypeptide indicated in (2) or (3) may be obtained by using, for example, site-directed mutagenesis to express a polynucleotide which encodes the fluorescent polypeptide indicated in the above (1) and which has a mutation artificially introduced therein. Examples of the site-directed mutagenesis encompass the Kunkel method (Kunkel et al. (1985): Proc. Natl. Acad. Sci. USA, vol. 82. p488-).

An example of the fluorescent polypeptide indicated in the above (2) or (3) is a fluorescent polypeptide having an amino acid sequence set forth in SEQ ID NO: 4. The fluorescent polypeptide having an amino acid sequence set forth in SEQ ID NO: 4 is one of the fluorescent protein clones obtained by isolation from *Cytaeis uchidae*, and is referred to as "CU 17S". StayGold is a mutant of CU 17S obtained by modifying CU17S, and has an amino acid sequence (amino acid sequence of CU17S) set forth in SEQ ID NO: 4, the amino acid sequence having amino acid 168 replaced from valine (V) to alanine (A) therein.

That is to say, the polypeptide of the present invention has another aspect, which is a fluorescent polypeptide indicated in any one of the following (4) to (6).

(4) A polypeptide having an amino acid sequence set forth in SEQ ID NO. 4;

(5) A polypeptide having an amino acid sequence set forth in SEQ ID NO: 4, the amino acid sequence having replaced, deleted, inserted, and/or added therein not less than 1 and not more than 32 amino acids. Note that the number of amino acids having been replaced, deleted, inserted and/or added is preferably not less than 1 and not more than 26, more preferably not less than 1 and not more than 21, more preferably not less than 1 and not more than 10, more preferably not less than 1 and not more than 8, even more preferably not less than 1 and not more than 6, and particularly preferably not less than 1 and not more than 4.

(6) A polypeptide having not less than 85% sequence identity with respect to an amino acid sequence set forth in SEQ ID NO: 4. Note that the sequence identity is preferably not less than 88%, more preferably not less than 90%, more preferably not less than 95%, more preferably not less than 96%, even more preferably not less than 97%, and particularly preferably not less than 98% or not less than 99%.

An example of the fluorescent polypeptide indicated in the above (2) or (3) has an amino acid sequence in which amino acid 168 of an amino acid sequence set forth in SEQ ID NO: 1 is alanine and which exhibits not less than 85% sequence identity with respect to an amino acid sequence set forth in SEQ ID NO: 1.

An example of the fluorescent polypeptide indicated in the above (2) or (3) is the fluorescent polypeptide having an amino acid sequence set forth in SEQ ID NO: 6.

The fluorescent polypeptide indicated in the above (2) or (3) may exhibit a fluorescence property equivalent to the fluorescence property represented by an amino acid sequence set forth in SEQ ID NO: 1. In the respect, exhibiting a "fluorescence property equivalent to" refers to having at least one selected from the group consisting of an excitation wavelength, a fluorescence wavelength, a pH sensitivity, photostability, a molar extinction coefficient, fluorescence quantum efficiency, an excitation spectrum shape or emission spectrum shape, an excitation wavelength local maximum and an emission wavelength local maximum, an excited-state lifetime, and a chromophore maturation rate that are equivalent to those of the fluorescent polypeptide represented by an amino acid sequence set forth in SEQ ID NO: 1. The phrase a "fluorescence property equivalent to" preferably refers to having (i) photostability and fluorescence brightness at the time of introduction into a cell and (ii) an equivalent quantum yield at the time of introduction into a cell.

Examples of the fluorescent polypeptide having an excitation wavelength equivalent to that of StayGold encompass, but not limited to, the one having a maximum excitation wavelength which falls within a range of 486 nm to 506 nm. Examples of the fluorescent polypeptide having a fluorescence wavelength equivalent to that of StayGold encompass, but not limited to, the one having a maximum fluorescence wavelength which falls within a range of 495 nm to 515 nm.

Fading of fluorescence over time is observed in fluorescent polypeptides. It becomes difficult to observe fluorescence as fading progresses.

The fluorescent polypeptide of the present invention has high photostability. The photostability of fluorescence can be evaluated with use of an index which is the degree to which fluorescence is less likely to fade. When photostability is higher, an effect of a longer observable time can be produced.

The fluorescent polypeptide of the present invention emits fluorescence which is less likely to fade. An example of the fluorescent protein of the present invention emits fluorescence which is less likely to fade and maintains a high fluorescence intensity for a long time, compared with publicly known fluorescent proteins. As an example, for the fluorescent polypeptide of the present invention, it takes preferably not less than 1,000 seconds and more preferably not less than 5,000 seconds for the number of emitted photons per molecule per second to decrease in half from 1,000 to 500, in accordance with the evaluation standard method of photostability.

The fluorescent polypeptide of the present invention, which emits fluorescence which is less likely to fade, can be suitably used in, for example, single-molecule imaging or an observation of fluorescence in a cell which expresses a small copy number of fluorescent polypeptides.

In addition, fluorescence of the fluorescent polypeptide of the present invention is bright. The absolute brightness of fluorescence can be evaluated with use of an index which is the product of the absolute molar extinction coefficient and the quantum efficiency of the fluorescence. Meanwhile, an actual brightness of fluorescence can be evaluated with use of an index which is the product of an effective molar extinction coefficient and the quantum efficiency of the fluorescence plus the maturation speed of a chromophore.

The absolute molar extinction coefficient ($M^{-1}cm^{-1}$) of the fluorescent polypeptide of the present invention is preferably not less than 100000, preferably not less than 120000, more preferably not less than 130000, even more preferably not less than 140000, and particularly preferably not less than 150000. Further, the quantum efficiency (D of the fluorescence is not less than 0.75 (75%), preferably not less than 0.80 (80%), and more preferably not less than 0.90 (90%).

As is indicated also in Examples, this value of the quantum yield is significantly higher than those of conventional green fluorescent proteins. When the quantum yield of fluorescence is higher, the fluorescence intensity is higher. This typically leads to brighter fluorescence, and is thus more suitable for use in fluorescence observation.

An example of the fluorescent polypeptide of the present invention exhibits higher photostability than EGFP, or has brighter fluorescence than EGFP.

In a fluorescent polypeptide, known as the amino acid sequence of a fluorescent polypeptide that forms a chromophore is X-Y-G (X represents any given amino acid). In the fluorescent polypeptide indicated in the above (1), the amino acid sequence of amino acids 57 to 59 in SEQ ID NO: 1 is G-Y-G. Thus, also in the fluorescent polypeptide indicated in the above (2) or (3), it is preferable that even when amino acid 57 of SEQ ID NO: 1 may be replaced, amino acids 58 and 59 be maintained without any mutation, and it is more preferable that all of amino acids 57 to 59 be maintained without any mutation.

The fluorescent polypeptide may be may be a monomer, or may be a multimer. For example, in a case of molecular labeling and in a case of a use for the probe of fluorescence resonance energy transfer (FRET), the fluorescent polypeptide is preferably a monomer. Both leucine (L) of amino acid 155 and tyrosine (Y) of amino acid 187 of an amino acid sequence set forth in SEQ ID NO: 1 are presumed to be involved in, in particular, the formation of a multimer of the fluorescent polypeptide.

Furthermore, leucine (L) of amino acid 135, proline (P) of amino acid 136, glutamic acid (E) of amino acid 138, isoleucine (I) of amino acid 142, arginine (R) of amino acid 144, leucine (L) of amino acid 155, cysteine (C) of amino acid 165, glutamic acid (E) of amino acid 167, tyrosine (Y) of amino acid 187, and tryptophan (W) of amino acid 189 of an amino acid sequence set forth in SEQ ID NO: 1 are all involved in dimerization of the fluorescent polypeptide, i.e., form an interface. It is therefore possible to monomerize the fluorescent polypeptide by replacing at least one of these amino acids with any other amino acid(s).

In order for the fluorescent polypeptide to be monomerized, at least one selected from the group consisting of leucine (L) of amino acid 155 and tyrosine (Y) of amino acid 187 of an amino acid sequence set forth in SEQ ID NO: 1 has been preferably subjected to amino acid replacement. In particular, in order for the fluorescent polypeptide to be monomerized, it is preferable that leucine (L) of amino acid 155 and tyrosine (Y) of amino acid 187 of SEQ ID NO: 1 have been replaced with threonine (T) and alanine (A), respectively. Examples of such a fluorescent polypeptide encompass: a fluorescent polypeptide having SEQ ID NO: 29, which is an amino acid sequence having leucine (L) of amino acid 155 replaced with threonine (T); and a fluorescent polypeptide having SEQ ID NO: 27, which is an amino acid sequence having tyrosine (Y) of amino acid 187 replaced with alanine (A). A base sequence which encodes a polypeptide of SEQ ID NO: 29 is indicated in SEQ ID NO: 30, and a base sequence which encodes a polypeptide of SEQ ID NO: 27 is indicated in SEQ ID NO: 28.

It is more preferable that, in addition to the replacements of leucine (L) of amino acid 155 and tyrosine (Y) of amino acid 187 of an amino acid sequence set forth in SEQ ID NO: 1, at least one amino acid selected from the group consisting of leucine (L) of amino acid 135, proline (P) of amino acid 136, glutamic acid (E) of amino acid 138, isoleucine (I) of amino acid 142, arginine (R) of amino acid 144, cysteine (C) of amino acid 165, glutamic acid (E) of amino acid 167, and tryptophan (W) of amino acid 189 of an amino acid sequence set forth in SEQ ID NO: 1 have been subjected to amino acid replacement. It is presumed that these amino acids are present at the interfacial surface of the protein of StayGold and have side chains which are directed towards the outside of the protein, and thus particularly affect multimerization. Accordingly, replacing these amino acids allows more stable monomerization of StayGold. Further, asparagine (N) of amino acid 132, proline (P) of amino acid 151, and lycine (K) of amino acid 162 are also present at the interfacial surface of the protein, and can affect multimerization.

As to the amino acid replacement that is presumed to affect the above multimerization of a protein, an amino acid present after the replacement is not particularly limited provided that the amino acid enables a desired effect to be obtained. For example, the amino acid replacement may be at least one selected from the group consisting of the replacement of leucine (L) of amino acid 135 with threonine (T), the replacement of proline (P) of amino acid 136 with tyrosine (Y), the replacement of glutamic acid (E) of amino acid 138 with glutamine (Q), the replacement of isoleucine (I) of amino acid 142 with threonine (T), the replacement of arginine (R) of amino acid 144 with threonine (T), the replacement of cysteine (C) of amino acid 165 with glutamine (Q), the replacement of glutamic acid (E) of amino acid 167 with alanine (A), and the replacement of tryptophan (W) of amino acid 189 with tyrosine (Y) that are made in an amino acid sequence set forth in SEQ ID NO: 1.

The number of mutations for monomerizing the fluorescent polypeptide is not particularly limited. For example, one or more, two or more, or three or more of the above mutations may be included. Alternatively, six or less, five or less, or four or less of the above mutations may be included.

A fluorescent polypeptide having an amino acid sequence set forth in SEQ ID NO: 6 has the replacement (referred to as H169Y) of histidine (H) of amino acid 169 with tyrosine (Y), the replacement (referred to as C174I) of cysteine (C) of amino acid 174 with isoleucine (I), and the replacement (referred to as C208I) of cysteine (C) of amino acid 208 with isoleucine (I) that have been made in SEQ ID NO: 1, and is thus a mutant (an H169Y/C174I/C208I mutant of StayGold) of the fluorescent polypeptide having an amino acid sequence set forth in SEQ ID NO: 6. This mutant, which has a small amount of cysteine, exhibits more stable folding in an oxidative state, and is thus useful also in, for example, labeling in the inner cavity of an endoplasmic reticulum. Furthermore, a mutant having the replacement of H169Y, C174I, or C208I is useful in that the fluorescent protein emits bright fluorescence. The mutant having the replacement of H169Y, C174I, or C208I may also have the mutation of L155T or Y187A.

[2. Polynucleotide which Encodes Fluorescent Polypeptide]

A polynucleotide of the present invention encodes any one of the above fluorescent polypeptides.

Specifically, the polynucleotide which encodes the fluorescent polypeptide is a polynucleotide set forth in any one of the following (1) to (3).

(1) A polynucleotide which encodes a polypeptide having an amino acid sequence set forth in SEQ ID NO: 1;

(2) a polynucleotide which encodes a polypeptide having an amino acid sequence set forth in SEQ ID NO: 1, the amino acid sequence having replaced, deleted, inserted, and/or added therein not less than 1 and not more than 32 amino acids, the polypeptide having a fluorescence property; and (3) a polynucleotide which encodes a polypeptide having not less than 85% sequence identity with respect to an amino acid sequence set forth in SEQ ID NO: 1 and having a fluorescence property. This polynucleotide has a sequence identity with respect to the polynucleotide base sequence set forth in the above (1) which is preferably not less than 88%, more preferably not less than 90%, preferably not less than 95%, more preferably not less than 96%, even more preferably not less than 97%, and particularly preferably not less than 98% or not less than 99%.

The polynucleotide of the present invention can be present in the form of RNA or in the form of DNA. An example of the form of RNA is mRNA. An example of the form of DNA is cDNA or genomic DNA. DNA may double-stranded or single-stranded.

Each of base sequences indicated in SEQ ID NO: 2 and SEQ ID NO: 3, which are examples of the polynucleotide of the present invention, is cDNA which encodes the fluorescent polypeptide indicated in SEQ ID NO: 1, and a base sequence indicated in SEQ ID NO: 5 is cDNA which encodes the fluorescent polypeptide indicated in SEQ ID NO: 4 and a base sequence indicated in SEQ ID NO: 7 is cDNA which encodes the fluorescent polypeptide indicated in SEQ ID NO: 6. Further, the polynucleotide of the present invention may include an additional sequence such as a sequence of an untranslated region (UTR).

A method for obtaining (isolating) the polynucleotide of the present invention is not particularly limited, but may be, for example, as follows: a probe which is specifically hybridized with a part of the base sequence of the polynucleotide is prepared and a genomic DNA library or a cDNA library is screened. Alternatively, the polynucleotide of the present invention may be synthesized according to a nucleic acid synthesis method such as a phosphoramidite method.

Examples of the method for obtaining the polynucleotide of the present invention encompass a method in which a nucleic acid amplification method such as PCR is used. For example, primers are prepared from the respective sequences (or the complementary sequences thereof) of the 5'-side and the 3'-side of the cDNA of the polynucleotide, and the primers are used to carry out PCR or the like with genomic DNA or cDNA being used as a template, so that a DNA region sandwiched between the primers is amplified. This makes it possible to obtain a large amount of DNA fragments which include the polynucleotide of the present invention.

[3. Vector, Expression Cassette]

The polynucleotide (e.g., DNA) of the present invention may be inserted into an appropriate vector to be used as a vector. The vector may be a kind of vector which replicates itself autonomously like a plasmid, or a kind of vector which is incorporated in a genome of the host cell when introduced into a host cell and is replicated together with a chromosome of the host cell.

The above vector is preferably an expression vector. In the expression vector, an element necessary for transcription, such as, for example, a promoter sequence, is functionally linked to the polynucleotide of the present invention. A promoter sequence is a DNA sequence that exhibits transcriptional activity in a host cell. The kind of the promoter sequence to be used may be selected as appropriate depending on the kind of the host cell and an intended use of the fluorescent polypeptide of the present invention. Example of the kind of the host cell encompass those described in, for example, [4. Transformant and method for preparing transformant].

A promoter sequence operable in a host cell is, for example, a promoter of *Bacillus stearothermophilus* maltogenic amylase gene, *Bacillus licheniformis* alpha-amylase gene, *Bacillus amyloliquefaciens* BAN amylase gene, *Bacillus Subtilis* alkaline protease gene, or *Bacillus pumilus* xylosidase gene; a PR promoter or PL promoter of phage lambda; a lac promoter, trp promoter, or tac promoter of *Escherichia coli*; or a polyhedrin promoter, P10 promoter, *Autographa californica* polyhedrosis basic protein promoter, baculovirus immediate-type early gene 1 promoter, baculovirus 39K delayed-type early gene promoter, promoter derived from yeast glycolysis gene, alcohol dehydrogenase gene promoter, TPI1 promoter, ADH2-4c promoter, ADH3 promoter, tpiA promoter, 35S promoter of cauliflower mosaic virus, SV40 promoter, MT-1 (metallothionein gene) promoter, cytomegalo promoter, or adenovirus 2 major late promoter.

In an expression vector, the polynucleotide of the present invention may be functionally bound as necessary to an appropriate terminator (e.g., polyadenylation signal, growth hormone terminator of a mammal, TPI1 terminator, or ADH3 terminator). The kind of the appropriate terminator may be selected as appropriate depending on the kind of the host cell.

The vector of the present invention may further include an element such as a transcription enhancer sequence.

The vector of the present invention may further include a DNA sequence that allows replication of the vector in the host cell. In a case where the host cell is a mammalian cell which expresses a Large T antigen, such a DNA sequence is, for example, an SV40 replication origin.

The vector of the present invention may further include a selective marker. Examples of the selective marker can encompass a drug resistance gene which is resistant to a drug such as ampicillin, kanamycin, tetracycline, chloramphenicol, neomycin, or hygromycin. These selective markers are applied to any kind of vector.

An expression cassette of the present invention refers to an expression cassette including (a) an expression regulatory region functional in an expression host and (b) the polynucleotide of the present invention. The expression cassette of the present invention may be in the form of the expression vector described above.

[4. Transformant and Method for Preparing Transformant]

(Transformant and Method for Preparing Transformant)

A transformant which includes the polynucleotide of the present invention, the expression cassette of the present invention, or the vector of the present invention can be prepared by introducing the polynucleotide of the present invention, the expression cassette of the present invention, or the vector of the present invention into an appropriate host cell. The prepared transformant contains the full length of the polynucleotide of the present invention or at least part of the polynucleotide, and allows expression of any one of the fluorescent polypeptides of the present invention. Similarly, progeny of the transformant of the present invention obtained with use of the transformant also contains the full length of the polynucleotide of the present invention or at least part of the polynucleotide, and allows expression of any one of the fluorescent polypeptides of the present invention. In the prepared transformant or progeny thereof, the full length or part of the polynucleotide of the present invention is preferably incorporated in a genome.

In the following description, the polynucleotide of the present invention, the expression cassette of the present invention, and the vector of the present invention are collectively referred to as a "foreign nucleic acid molecule" of the present invention. A method for introducing the foreign nucleic acid molecule of the present invention into a host cell may be selected depending on the kind of the host cell, as will be exemplified later. Further, a method for obtaining progeny of the transformant of the present invention may be selected depending on the kind of the transformant.

Examples of the host cell encompass a bacterial cell, a yeast cell, a fungal cell other than a yeast cell, and a higher eukaryotic cell. Examples of the higher eukaryotic cell encompass a plant cell and an animal cell. Examples of the animal cell encompass an insect cell, an amphibian cell, a reptile cell, an avian cell, a fish cell, and a mammalian cell. Examples of the bacterial cell encompass a Gram-positive bacterium such as *Bacillus* and *Streptomyces*; and a Gram-negative bacterium such as *Escherichia coli*. Examples of the yeast cell encompass a cell belonging to *Saccharomyces* or *Schizosaccharomyces*, such as, for example, *Saccharomyces cerevisiae* and *Saccharomyces kluyveri*. Examples of the fungal cell other than a yeast cell encompass a filamentous fungus cell. Examples of the filamentous fungus cell encompass a filamentous fungus cell belonging to *Aspergillus, Neurospora, Fusarium*, or *Trichoderma*. Examples of the insect cell encompass a silkworm cell. Examples of the mammalian cell encompass HEK293 cell, HeLa cell, COS cell, BHK cell, CHL cell, or CHO cell.

The method for transformation of a host cell may be selected as appropriate depending on, for example, the kind of the host cell. Examples of the method encompass protoplast method, method involving use of a competent cell, electroporation method, spheroplast method, acetic acid lithium method, calcium phosphate method, lipofection method, *Agrobacterium* method, and particle gun method. Examples of another method for transformation of a host cell encompass a method of performing transformation by producing a host cell which has an foreign nucleic acid molecule of the present invention incorporated in a chromosome thereof. The incorporation of a foreign nucleic acid molecule into a host chromosome can be performed by, for example, homologous recombination or heterologous recombination. Examples of still another method for transformation of a host cell encompass a method of (i) cotransfecting the foreign nucleic acid molecule of the present invention and a baculovirus into a host cell to produce a recombinant baculovirus in a culture supernatant of the host cell and then (ii) causing the host cell to be infected with the recombinant baculovirus, to cause the host cell to produce the fluorescent polypeptide of the present invention. Examples of the method for cotransfection encompass a calcium phosphate method and a lipofection method.

The transformant is cultured or cultivated under conditions that allow expression of the introduced foreign nucleic acid molecule.

The form of the transformant is not limited to a cell. Specifically, the transformant may be, for example, tissue, organ, or an individual organism that has been transformed with use of the foreign nucleic acid molecule of the present invention. In some cases, the transformant other than a cell is preferably of a non-human origin, and in particular, in a case where the transformant is an individual organism, the transformant is preferably of a non-human origin. The individual organism that has been transformed and that is of a non-human origin is referred to as a "non-human transgenic organism".

(Non-Human Transgenic Organism and Method for Preparation Thereof)

A non-human transgenic organism of the present invention is, for example, a higher organism. Examples of a transgenic plant encompass transgenic forms of dicotyledons including *Arabidopsis thaliana*; and monocotyledons such as *Brachypodium distachyon*, rice, wheat, and barley. Examples of a transgenic animal encompass transgenic forms of animals such as zebrafish, mouse, rat, and pig.

A method for preparing a non-human transgenic organism of the present invention may be selected depending on the kind of the transgenic organism. Examples of a method for preparing a transgenic animal encompass methods such as: a method of introducing in vitro a foreign nucleic acid molecule of the present invention into a fertilized egg collected from a donor organism, according to a microinjection method or the like; and a method of causing in vitro a cell of an early embryo in development derived from a donor organism to be infected with a viral vector such as a retrovirus. A method for preparing a transgenic plant may be a method of introducing the foreign nucleic acid molecule of the present invention into a plant cell according to, for example, the *Agrobacterium* method; a particle gun method; an electroporation method; or the like, and then carrying out, as necessary, a process of the formation of a callus, so that an individual transgenic plant is obtained.

A method for obtaining progeny of the non-human transgenic organism of the present invention may also be selected depending on the kind of the non-human transgenic organism. In a case of higher organisms, examples of such a method encompass a method of obtaining progeny through breeding. In a case of a plant among higher organisms, the progeny may be obtained with use of an asexual reproduction technique suitable for the kind of the plant.

(Clone of Non-Human Transgenic Organism and Method for Preparing Clone)

The present invention encompasses in its scope, for example, using a non-human transgenic organism of the present invention to prepare a clone of the non-human transgenic organism. Like the non-human transgenic organism from which the clone is prepared, the prepared clone contains in a genome the full length of a polynucleotide of the present invention or at least part of the polynucleotide, and allows expression of any one of the fluorescent polypeptides of the present invention. The concept of the "clone" covers an embryonic cell clone and a somatic cell clone.

Examples of a method for preparing a clone encompass a nuclear transplantation method of transplanting a cell nucleus of a donor into an enucleated unfertilized egg which serves as a recipient. Examples of the cell nucleus of a donor encompass (1) a somatic cell nucleus of the non-human transgenic organism from which a clone is produced or (2) an embryonic cell nucleus derived from the non-human transgenic organism from which a clone is produced. The cell nucleus of a donor contains in a genome the full length of a polynucleotide of the present invention or at least part of the polynucleotide.

A method for transplanting the cell nucleus of a donor is not particularly limited. Example of the method encompass (1) a method of cell fusion between an enucleated unfertilized egg and a donor cell and (2) a method of introducing a donor cell into an enucleated unfertilized egg without carrying out cell fusion.

[5. Fusion Polypeptide of Present Invention, Recombinant Antibody Having any Antigen Protein Linked to Fluorescent Polypeptide in a Genetically Engineered Manner]

(Fusion Polypeptide)

A fusion polypeptide (hereinafter referred to as a fusion polypeptide of the present invention) that includes the fluorescent polypeptide of the present invention and another polypeptide is also within the scope of the present invention. Examples of the fusion polypeptide encompass: a fusion protein produced by expression of the expression cassette and/or vector of the present invention; a fusion protein in which any protein is labeled with the fluorescent polypeptide of the present invention; a fusion polypeptide obtained by fusing together the fluorescent polypeptide of the present invention and a predetermined peptide sequence for stabilizing fluorescence; and an FRET probe which includes the fluorescent polypeptide of the present invention and another fluorescent polypeptide. That is to say, the kind of another polypeptide to be fused with the fluorescent polypeptide of the present invention is not particularly limited.

A fusion polypeptide having both the N terminus and the C terminus or either the N terminus or the C terminus of the fluorescent polypeptide of the present invention linked to any other polypeptide therein is also within the scope of the present invention. The any other polypeptide to be linked is not limited to any length or sequence.

In an example of the fusion protein of the present invention, both the N terminus and the C terminus or either the N terminus or the C terminus of the fluorescent polypeptide of the present invention is/are linked to the any other polypeptide via an insertion sequence which consists of any amino acid sequence. Another example of the fusion protein of the present invention includes an insertion sequence which consists of any amino acid sequence and which is interposed between any adjacent amino acids of amino acids 1 to 5 of the N terminus of the fluorescent polypeptide of the present invention.

Each of these insertion sequences can be an amino acid sequence which consists of not less than three, not less than five, not less than seven, or not less than ten amino acids. Alternatively, the insertion sequence can be an amino acid sequence which consists of not more than 30, not more than 20, or not more than 15 amino acids.

As an example, a fusion protein having the C terminus of the fluorescent polypeptide of the present invention and any other polypeptide linked together therein is a fusion protein having the C terminus of the fluorescent polypeptide of the present invention and any other polypeptide linked together via an amino acid sequence (referred to as an insertion sequence c4) which consists of 10 amino acids set forth in SEQ ID NO: 8.

As another example, a fusion protein having either the N terminus or the C terminus of the fluorescent polypeptide of the present invention and any other polypeptide linked together therein is a fusion protein having an amino acid sequence (referred to as insertion sequence n1 or n2) which consists of nine amino acids described in SEQ ID NO: 9 or SEQ ID NO: 10 interposed between any adjacent amino acids of amino acids 1 to 5 of the N terminus of a fluorescent polypeptide of the present invention. Examples of such a fusion protein encompass: a fusion protein having the insertion sequence n1 (SEQ ID NO: 9) interposed between amino acid 4 and amino acid 5 of the N terminus of the fluorescent polypeptide of the present invention; and a fusion protein having the insertion sequence n2 (SEQ ID NO: 10) interposed between amino acid 3 and amino acid 4 of the fluorescent polypeptide of the present invention. Note that examples of the fusion protein also encompass a fusion protein which has both an insertion sequence c4 and the insertion sequence n1 or n2. Having the insertion sequences described above makes it possible to improve the photostability of a fusion protein.

In a case where both the N terminus and the C terminus or either the N terminus or the C terminus of the fluorescent polypeptide of the present invention and any other polypeptide are linked together via an insertion sequence that consists of any amino acid sequence, it is possible to obtain more stable fluorescence than in a case where any other polypeptide is directly bound to the fluorescent polypeptide of the fluorescent polypeptide.

Still another example of the fusion protein includes two or more fluorescent polypeptides of the same kind or of different kinds of the present invention that are linked together, i.e., a tandem dimer having two fluorescent polypeptides of the same kind or different kinds of the present invention linked together, or a fusion protein having three or more fluorescent polypeptides of the same kind or different kinds of the present invention linked together. Such a tandem dimer of the fluorescent polypeptides of the present invention and the fusion protein having three or more fluorescent polypeptides of the present invention linked together therein may have the fluorescent polypeptides linked together therein via an insertion sequence having any sequence. An insertion sequence may be included, the insertion sequence consisting of any amino acid sequence and being interposed between any adjacent amino acids of amino acids 1 to 5 of the N terminus of the fluorescent polypeptide of the present invention. The insertion sequence is not limited to any amino acid sequence and any amino acid sequence length, but, for example, has not less than 10 amino acids and not more than 150 amino acids. The insertion sequence as described above may be applied. In addition, any other polypeptide may be further added to both the N terminus and the C terminus or either the N terminus or the C terminus of the fluorescent polypeptides linked together. The added polypeptide is not limited to any amino acid sequence or any amino acid sequence length, but has, for example, not less than 5 amino acids and not more than 20 amino acids.

In the tandem dimer and the fusion protein having three or more fluorescent polypeptides linked together therein, the amino acid sequences of respective proteins may be bound together via a publicly known linker sequence serving as an insertion sequence. For example, with use of an EV linker, an alpha linker, or any other linker selected depending on the purpose, the respective amino acid sequences may be bound together.

Examples of the tandem dimer having two fluorescent polypeptides of the present invention linked together encompass: a tandem dimer (referred to as tdStayGold) having the amino acid sequence of SEQ ID NO: 13; a tandem dimer (referred to as tdStayGold (long)) having the amino acid sequence of SEQ ID NO: 15; a tandem dimer (referred to as tdoxStayGold) having the amino acid sequence of SEQ ID NO: 17, and a tandem dimer (referred to as tdStayGold alpha) having the amino acid sequence of SEQ ID NO: 19. A base sequence which encodes the polypeptide indicated in SEQ ID NO: 13 is indicated in SEQ ID NO: 14, a base sequence which encodes the polypeptide indicated in SEQ ID NO: 15 is indicated in SEQ ID NO: 16, a base sequence which encodes the polypeptide indicated in SEQ ID NO: 17 is indicated in SEQ ID NO: 18, and a base sequence which encodes the polypeptide indicated in SEQ ID NO: 19 is indicated in SEQ ID NO: 20. Examples of another example of the tandem dimer having two fluorescent polypeptides of the present invention linked together encompass a tandem dimer having an amino acid sequence exhibiting a sequence identity with respect to the amino acid sequences of the tandem dimers exemplified above which is not less than 85%, not less than 88%, not less than 90%, not less than 95%, not less than 96%, not less than 97%, not less than 98%, or not less than 99%.

The fusion polypeptide of the present invention may be fluorescent polypeptide chemically synthesized or produced with use of genetic recombination technology, by the same method that the fluorescent polypeptide of the present invention is synthesized or produced.

A fusion protein in which the above-described tandem dimer having two fluorescent polypeptides of the present invention linked together is fused with a target protein the visualization of which is desirable can be suitably used for a dynamics analysis through the observation of fluorescence within the cell of the target protein.

(Antibody)

A recombinant antibody having any antigen protein linked to the fluorescent polypeptide of the present invention in a genetically engineered manner therein is also within the scope of the present invention. Note that the antibody may be an antibody fragment which maintains the ability to bind specifically to an antigen.

[6. Pluripotent Stem Cell and Method for Preparing Pluripotent Stem Cell]

The present invention also covers a method for preparing a pluripotent stem cell from a cell of the non-human transgenic organism of the present invention. The method for producing a pluripotent stem cell includes a step (reprogramming step) of introducing a reprogramming factor into a cell (which can also be referred to as a "starting cell") collected from the non-human transgenic organism of the present invention or treating such a cell with a reprogramming factor, to prepare a pluripotent stem cell. The non-human transgenic organism is, for example, a non-human transgenic higher animal and is, in particular, a non-human transgenic mammal.

(Obtained Pluripotent Stem Cell)

An obtained pluripotent stem cell at least exhibits multipotency, and more preferably exhibits a state of exhibiting pluripotency or a state prior to the state of exhibiting pluripotency. In the present invention, the term "multipotency" refers to the ability to differentiate into certain cell species such as, for example, a nervous system and a hematopoietic system. Further, in the present invention, the term "pluripotency" refers to the ability to differentiate into any of the cells and tissue that constitute an individual organism, although incapable of constituting the individual organism itself. An example of the obtained pluripotent stem cell is a so-called "induced pluripotent stem cell". An "induced pluripotent stem cell" is a cell having properties close to those of an ES cell (embryonic stem cell). More specifically, the "induced pluripotent stem cell" encompasses an undifferentiated cell that has pluripotency and the ability to proliferate in undifferentiated state, depending on the culture conditions.

[7. Method for Observing Fluorescence]

The fluorescent polypeptide or fusion polypeptide of the present invention are not limited to any particular uses, but can be widely used for fluorescence observation. The method for observing fluorescence includes a producing step of producing a polypeptide or fusion polypeptide of the present invention in a cell, an excitation light irradiating step of irradiating the cell with excitation light, and an observing step of observing fluorescence originating from the polypeptide or the fusion polypeptide.

The producing step can be carried out by, for example, the method described in the section [4. Transformant and method for preparing transformant] above. The fluorescence observing step is a step of observing fluorescence emission emitted from the polypeptide or fusion polypeptide of the present invention. The observing step is carried out by detecting fluorescence emission emitted from the polypeptide or fusion polypeptide of the present invention. A method for detecting fluorescence is not particularly limited, but examples of fluorescence detecting means encompass a UV transilluminator or LED transilluminator, a fluorescence microscope, a fluorescence detector, and flow cytometry. Examples of the most preferable means encompass a fluorescence microscope, single-molecule imaging (total reflection illumination TIRFM) and a light-sheet microscope. Examples of a more or less preferable means encompass a structured illumination microscope (SIM) and a Nipkow disk confocal (multifocal) microscope. With use of the above fluorescence detecting means, the presence or absence of fluorescence emission, a distribution of fluorescence emission, or a fluorescence intensity may be measured temporarily or over time.

As to an excitation light irradiating scheme in the excitation light irradiating step, it is preferable to use Kohler illumination as, for example, illumination of an object with use of an objective lens of a microscope Using Kohler illumination yields a higher photostability effect of the fluorescent polypeptide of the present invention than using critical illumination.

In the observing step, fluorescence originating from a polypeptide of a fusion polypeptide may be observed by taking two or three dimensional, still or moving images.

Further, in the analysis or processing of the still or moving images of fluorescence that have been taken, information processing may be carried out with use of an appropriate information processing technique. For example, it is possible to accumulate large amounts of still or moving image information to adopt a process of carrying out artificial intelligence machine learning (AI learning).

Examples of another fluorescence observation encompass a method which includes a step (introducing step) of introducing the fluorescent polypeptide or fusion polypeptide of the present invention into a cell and the "fluorescence observing step" above. Examples of a method for introducing a fluorescent polypeptide or the like in a cell encompass a microinjection method of injecting purified fluorescent polypeptide or the like into a cell.

One of the purposes of fluorescence observation is analysis of localization or dynamics of a polypeptide. By using a fusion polypeptide having the fluorescent polypeptide of the present invention and another polypeptide (referred to as polypeptide X) fused together in a genetically engineered manner therein, it is possible to visualize and thus analyze the localization or dynamics of the polypeptide X in a cell. The polypeptide X is not limited to any particular kind, but examples thereof encompass a protein localized in a cell, a protein specific to an organelle, and a targeting signal. Examples of the targeting signal encompass a nuclear localization signal, a mitochondrial localization signal, a plasma membrane localization signal, and endoplasmic reticulum localization signal.

Another purpose of fluorescence observation is analysis of expression of a target gene. By carrying out the producing step above under control of the expression regulatory sequence of the target gene, it is possible to measure activity of the expression regulatory sequence. The activity of the expression regulatory sequence of a target gene reflects the expression level of the target gene.

[8. Method for Preparing Fluorescent Polypeptide]

The present invention also provides a method for preparing a mutant fluorescent polypeptide on the basis of a fluorescent polypeptide having an amino acid sequence set forth in SEQ ID NO: 1, 4, or 6.

Specifically, an aspect of the method, in accordance with the present invention, for preparing a fluorescent polypeptide includes:

(i) a step of preparing a mutant polypeptide having mutated therein at least one of the amino acids of an amino acid sequence set forth in SEQ ID NO: 1, 4, or 6 except amino acids 58 and 59;

(ii) a comparing step of comparing the fluorescence property of the mutant polypeptide with the fluorescence property of a polypeptide exhibited before the mutation; and (iii) a selecting step of selecting a mutant polypeptide the fluorescence property of which has found to change compared with the fluorescence property exhibited before the mutation in the comparing step.

In the step of preparing a mutant polypeptide, -Y-G of an amino acid sequence X-Y-G (X indicates any amino acid), which forms a chromophore, is fixed, and the other amino acids are mutated. This makes it possible to efficiently produce a mutant polypeptide which maintains a fluorescence property. For the number of amino acids to be mutated and a method for mutating an amino acid in each of SEQ ID NO: 1, SEQ ID NO: 4, and SEQ ID NO: 6, see, for example, the description in the section [1. Polypeptide having fluorescence property] above.

In addition, in the selecting step above, a mutant polypeptide which has a fluorescence property that has changed is selected, and a mutant polypeptide which has completely lost a fluorescence property is removed.

It can be understood that the above method for preparing a mutant fluorescent polypeptide is a method of screening mutant fluorescent polypeptides.

[9. Kit of Present Invention]

(Kit)

A kit of present invention includes at least one selected from the group consisting of (1) the fluorescent polypeptide of the present invention, (2) the polynucleotide of the present invention, the nucleotide encoding a fluorescent polypeptide, (3) the expression cassette of the present invention, (4) the vector of the present invention, (5) the transformant of the present invention, and (6) the fusion polypeptide of the present invention. In a case where the polynucleotide of (2) above is RNA, the kit can be applied to an individual organism such as a human, as a kit for temporary expression involving no genome gene recombination.

The kit of the present invention can be prepared with use of materials and techniques publicly known in the related technical field. A reagent for a fluorescent polypeptide, a polynucleotide, etc. can be prepared in a form suitable for preservation, by dissolving the reagent in a suitable solvent. The solvent can be water, ethanol, or any other kinds of publicly known buffer solutions.

The kit of the present invention may further include, as necessary, at least one selected from the group consisting of, for example, various reagents, instruments (e.g., a buffer solution, a test tube, and a pipet), and an instruction manual for the kit. The instruction manual for the kit has recorded thereon information about, for example, a detection method of the present invention, the detection method being described in [7. Observation, etc. with use of fluorescent polypeptide] above. The kit is used for reagent purposes or diagnosis purposes, for example.

The present invention is not limited to the embodiments, but can be altered by a skilled person in the art within the scope of the claims. The present invention also encompasses, in its technical scope, any embodiment derived by combining technical means disclosed in differing embodiments.

The present invention will be described in detail through the examples below. However, the present invention is not limited to the examples.

EXAMPLES

1. Cloning of Gene Derived from *Cytaeis uchidae*

(Materials and Method)

RNA was extracted from *Cytaeis uchidae* (scientific name; *Cytaeis uchidae* Rees, 1962) (phylum Cnidaria, Hydrozoa, Anthomedusae, Cytaeidae, *Cytaeis*). With use of total RNA derived from *C. uchidae*, RNA sequencing and the subsequent anchored PCR analysis were carried out. The details are as follows.

It was found that Unigene (#1784) encoded a polypeptide containing a GFP like domain. The polypeptide included two GYG sequences considered to be involved in chromophore synthesis. This polypeptide was used as a template, to carry out 5'-RACE-PCR with use of a CU17 5' RACE primer. As a result, an extension toward the N terminus so as to have a further GYG sequence was found. Next, an RT-PCR with use of a CU17 1st_Fwd primer and a CU17 Rev primer was carried out. As a result, two RNA transcripts which encode different polypeptides (named CU17L and CU17S) were obtained.

CU17L was expected to correspond to a protein product of #1784 and be a fluorescent protein of three domains. However, CU17L itself did not emit fluorescence in the expression system used by the inventors. In addition, when the three domains were separately expressed, none of the domains emitted fluorescence. Meanwhile, CU17S was expected to correspond to a fluorescent protein of a single domain. Interestingly, the N terminus region (approximately three fourths of the full length of the protein) of CU 17S had 84.8% sequence identity with respect to the region to which the 1st repeat of CU17L corresponded. Further, the C terminus region (approximately one fourth of the full length of the protein) of CU17S had 93.3% sequence identity with respect to the region to which the 3rd repeat of CU17L corresponded. For the purpose of investigating the existence of the transcript of CU17S, the 3'-side of the RT-PCR product was extended with use of a CU17 3' RACE primer, and furthermore, the 5'-side of the RT-PCR product was extended with use of a CU17 5' RACE-5 primer. These anchored PCR and RT-PCR analyses were carried out with use of total RNA prepared from #17 strain of *C. uchidae*.

(Result)

As a result of the above cloning, a transcript was identified, the transcript being considered to encode a fluorescent protein having a tripeptide GYG which forms a chromophore in an appropriate position. This clone was named CU17S. The amino acid sequence of CU17S is indicated in SEQ ID NO: 4, and the base sequence of a gene coding region is indicated in SEQ ID NO: 5. CU17S was found to have completely novel primary structure. Even ObeCFP, which is a homologue having the highest sequence identity with respect to CU17S, had only 15.2% sequence identity. From the alignment of amino acid sequences (see also FIG. 4, which will be described later), it can be understood that CU17S has a β-can structure similar to the other fluorescent proteins.

2. Expression of CU17S Protein in *Escherichia coli*

(Materials and Method)

<Expression of *Escherichia coli* Expression Vector in *Escherichia coli*, Culture, and Protein Purification>

After cDNA was inserted in an *Escherichia coli* expression vector (pRSETB), the vector was introduced in *Escherichia coli* (JM109 (DE3)) and the *Escherichia coli* was cultured, so that a colony was obtained. The obtained colony was irradiated with light, with use of a UV illuminator, a blue LED, and a green LED individually, to see whether fluorescence was emitted.

In addition, an *Escherichia coli* expression plasmid DNA which has a histidine tag added at the N-terminus of the CU17S protein was established, the transformation of *Escherichia coli* was carried out, and one-step purification was carried out with use of an Ni-NTA column. Next, a buffer exchange was carried out with use of a Sephadex G-25 column.

(Result)

A colony which emitted green fluorescence was obtained, and a clone of the fluorescent protein was obtained from this colony. As a result of expressing the CU17S protein in *Escherichia coli*, a sufficient amount of purified protein was obtained.

3. Analysis of Fluorescence Property of CU17S (Materials and Method)

<Measurement of Absorption Spectrum, Fluorescence Spectrum, and Quantum Yield of CU17S>

For the purpose of analyzing the fluorescence property of CU17S obtained in the above-described [1.] and [2.], an absorption spectrum, a fluorescence spectrum, and a quantum yield were measured.

The excitation spectrum and fluorescence spectrum were measured via a spectrofluorophotometer F-4500 (Hitachi High-Technologies Corporation) (excitation wavelength: 475 nm, fluorescence wavelength: 550 nm). The absorption spectrum was measured via a spectrophotometer U-2910 (Hitachi High-Technologies Corporation). The quantum yield was measured via an absolute PL quantum yield measuring system, Quantaurus-QY (Hamamatsu Photonics K.K.) (excitation wavelengths: 470 nm, 480 nm).

(Result)

FIG. 1 is a diagram illustrating a fluorescence excitation spectrum and a fluorescence emission spectrum observed in *C. uchidae*. The fluorescence excitation spectrum of CU17S had a shoulder at around 450 nm and exhibited the main peak at 496 nm. This was identical to the fluorescence property (FIG. 1) observed in *C. uchidae*.

4. Analysis of Photostability of CU17S (Materials and Method)

A HeLa cell was transfected with a gene of CU 17S, with use of Lipofectamine 2000 reagent. One day after the transfection, photostability was investigated. The measurement conditions were as follows.

Buffer: HBSS containing 15 mM of HEPES-NaOH (pH 7.4); Cooled CCD camera (ORCA-AG, Hamamatsu Photonics); Fluorescence filter cube: Exciter: 488.0 IF 10 (488±5 nm) (Cheshire Optical); Dichroic mirror: DM500 (Olympus); Emitter: BA520IF (520 nm<) (Olympus) combined with NDX001 (1% transmittance) (Asahi Spectra); Objective lens: 60× objective lens (UPlanSApo 60× oil, N.A. 1.35)

(Result)

In a case where CU17S was expressed in a HeLa cell, green fluorescence of CU 17S was localized in the cytoplasm section and in the nucleus section. As a result of quantitative observation with use of a fluorescence microscope, despite an insufficient maturity of the chromophore of CU17S in both *Escherichia coli* and a mammalian cell, green fluorescence did not substantially faded.

However, since it is typically believed that there is a negative correlation between the brightness (maturity) and photostability of a fluorescent protein, it was considered that an improvement in the maturity of the chromophore was not expected while the excellent photostability of CU17S was maintained.

5. Preparation of Mutant Based on CU17S (Materials and Method)

A CU17S mutant was prepared through random mutation. Primers used in the preparation of the mutant are indicated in SEQ ID NO: 11 and SEQ ID NO: 12.

(Result)

A mutant protein was obtained in which valine of amino acid 168 of the amino acid sequence of CU17S had been replaced with alanine.

The CU17S/V168A protein was expressed in *Escherichia coli* and purified, by the same method for CU 17S described above. As a result, a huge amount of CU17S/V168A protein was successfully produced and purified. The CU17S/V168A mutant was named StayGold. The amino acid sequence of StayGold is indicated in SEQ ID NO: 1, and the base sequence of a gene coding region is indicated in SEQ ID NO: 2. A base sequence having the codon usage of StayGold humanized therein is indicated in SEQ ID NO: 3.

6. Analysis of Fluorescence Property of StayGold (CU17S/V168A Mutant)

(Materials and Method)

With use of the obtained fluorescent protein of StayGold (CU 17S/V168A mutant), the fluorescence property was analyzed by the same method that is described in the section [3.].

Figure 2:
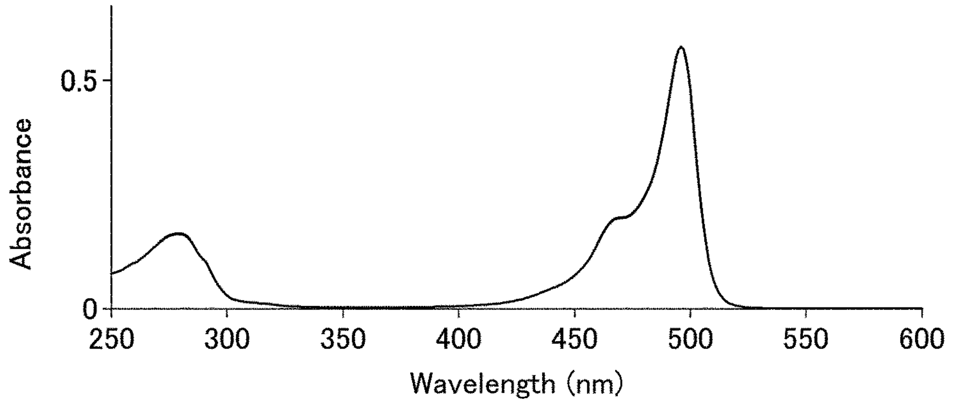
FIG. 2 is a diagram illustrating an absorption spectrum of StayGold (CU17S/V168A) in accordance with Examples of the present invention.

(Result) FIG. 2 is a diagram illustrating an absorption spectrum of StayGold (CU17S/V168A mutant). The absorption spectrum of CU17S/V168A had a high peak at 496 nm, and the absolute extinction coefficient at this wavelength was 159,000 $M^{-1}\cdot cm^{-1}$.

Figure 3:
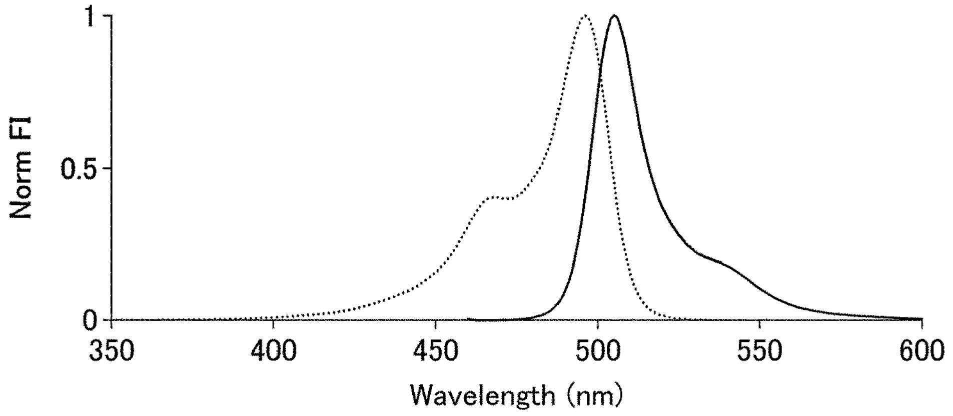
FIG. 3 is a diagram illustrating a fluorescence excitation spectrum and an emission spectrum of StayGold (CU17S/V168A) in accordance with Examples of the present invention.

FIG. 3 is a diagram illustrating a fluorescence excitation spectrum and a fluorescence emission spectrum of StayGold (CU17S/V168A mutant). The two respective graphs in FIG. 3 represent the excitation spectrum (indicated by a dotted line) and fluorescence emission spectrum (indicated by a solid line) of StayGold.

The fluorescence excitation spectrum and fluorescence emission spectrum of CU17S/V168A were the same as those of CU17S, and the quantum yield (D of CU17S/V168A was 0.93. This V168A mutation improved both protein expression and chromophore maturation.

FIG. 4 is an alignment of the amino acid sequences of StayGold, CU17S, and EGFP proteins of the present invention.

The measurement results of these fluorescent proteins are shown in Table 1.

TABLE 1

| | | | | | | | | Photostability $t_{1/2}$ (sec)[g] | | | |
|---|---|---|---|---|---|---|---|---|---|---|---|
| | | ε[c] | | | Brightness | | | | Expression in | | Protein[h] |
| | λab[a]/λem[b] | ($10^3$ $M^{-1}$ $cm^{-1}$) | | | | Cell[f] | | | living cell | | yield |
| Protein | (nm) | λab | 488 | $QY_f$[d] | Molecule[e] | CT | eCE | Protein | HBSS | DMEM | (mg/L) |
| StayGold | 496/505 | 159 | 105 | 0.93 | 148 | 1.88 | 2.06 | 11,487 | 9,919 | 12,421 | 194 |
| EGFP | 488/509 | 51 | 51 | 0.71 | 36 | 1.00 | 1.00 | 700 | 493 | 481 | 93 |
| SiriusGFP | 502/516 | 54 | 35 | 0.19 | 10 | 0.46 | 0.45 | 477 | 522 | 558 | 127 |
| mClover3 | 505/518 | 99 | 52 | 0.84 | 83 | 1.31 | 1.73 | 289 | 116 | 66 | 137 |
| mNG | 505/518 | 112 | 64 | 0.87 | 97 | 1.11 | 2.05 | 176 | 265 | 335 | 172 |

Superscript [a]λab: absorption peak wavelength (nm)

Superscript [b]λem: maximum fluorescence wavelength

Superscript [c]ε: molar extinction coefficient ($M^{-1}cm^{-1}$), the value of a molar extinction coefficient at an absorption peak wavelength is indicated. Indicated in the parentheses is the value of the molar extinction coefficient at 488 nm (the center wavelength of an excitation band-pass filter).

Superscript [d]$QY_f$: fluorescence quantum yield (%), the absolute value was measured with use of an absolute PL quantum yield measurement C9920-02 (Hamamatsu Photonics).

Superscript [e]a numerical value which is determined by ε × $QY_f$ and which represents the absolute brightness of a fluorescent protein.

Superscript [f]the brightness of a fluorescent protein in a HeLa cell 30 hours after cDNA transfection. The value of each green fluorescent protein was corrected with the value of mCherry, and was normalized on the basis of the value of an EGFP.

eCE: Equimolar coexpression of a green fluorescent protein and mCherry due to the use of bicistronic expression system.

Superscript [g]time required for a fluorescence emission rate to decrease from 1,000 photons/s per molecule to 500 photons/s per molecule.

Superscript [h]a total amount of purified protein collected from one liter of the culture solution of *Escherichia coli*.

mNG: mNeonGreen

From these results, it has been shown that StayGold is superior in brightness to publicly known bright green fluorescent proteins such as EGFP and mNeonGreen. In addition, StayGold was found to have remarkably excellent photostability.

7. Analysis of Photostability of StayGold (Purified Protein)

(7-1. Comparisons with Green Fluorescent Proteins)

Photostability was compared between StayGold and each of four previously-reported green fluorescent proteins: EGFP, SiriusGFP, mNeonGreen, and mClover3. SiriusGFP was an EGFP mutant which has been reported in recent years and which has an improved photostability. SiriusGFP has increased photostability which is twice as high as that of EGFP but exhibits decreased brightness which is three times as low as that of EGFP.

(Materials and Method)

Five kinds of fluorescent proteins were processed in a completely concurrent manner, under the same conditions. The fluorescent proteins were expressed in *Escherichia coli* and purified. As a result, StayGold was the most high-yielding fluorescent protein. The concentration of a soluble fraction was approximately 200 mg per liter of culture medium (Table 1).

<Measurement of Protein Concentration>

The measurement was carried out with use of a Bradford assay kit.

<Observation of Photobleach>

A solution of 1 μM fluorescent protein dispersed in a polyacrylamide gel was prepared. A solution-gel mixture was sandwiched between two cover glasses, and was subjected to a fading imaging experiment in which arc light irradiation (5.6 $W/cm^2$) was used.

As an evaluation method, a standard method for evaluating fluorescent proteins was used. First, the molar extinction coefficients of EGFP, SiriusGFP, mNeonGreen, and mClover3 at an irradiation light center wavelength of 488 nm were calculated. The density of photons reaching a sample was calculated from the irradiance (5.6 $W/cm^2$). Further, in consideration of the quantum yield of fluorescence of a fluorescent protein, the normalized fading curves of the five kinds of fluorescent proteins were obtained.

A change in fluorescence intensity associated with fading was measured with use of a fluorescence microscope (IX81, Olympus) and an image analysis device (AQUACOSMOS, Hamamatsu Photonics). As an excitation light source, a xenon lamp (75 W) was used. The excitation wavelength was adjusted via a band-pass filter to have a center wavelength of 488 nm and a half-value breadth of 10 nm, and this excitation light was applied, through an objective lens (UPlanSApo 40×, NA 0.95), to a sample of the fluorescent protein solution placed on a stage. A fluorescent image of the sample was captured on a cooled CCD camera (ORCA-AG, Hamamatsu Photonics) through a 520 nm long pass filter. The excitation light was applied continuously for 90 minutes, and an image of fluorescence was captured every 6 seconds. The average of the luminances of a circular area (a diameter corresponding to 115 pixels) in the central portion of the obtained image was determined, and from this determined average, the luminance of the fluorescence obtained from a sample containing no fluorescent protein was subtracted as background light. By plotting the luminances of the images of the respective time points, an attenuation curve due to fading of fluorescence was obtained.

(Result)

FIG. 5 is a diagram illustrating a simple comparison of a change in fluorescence intensity over time among the five kinds of green fluorescent proteins. According to this simple comparison, StayGold was brighter and was significantly higher in photostability than the other fluorescent proteins.

Figure 6:
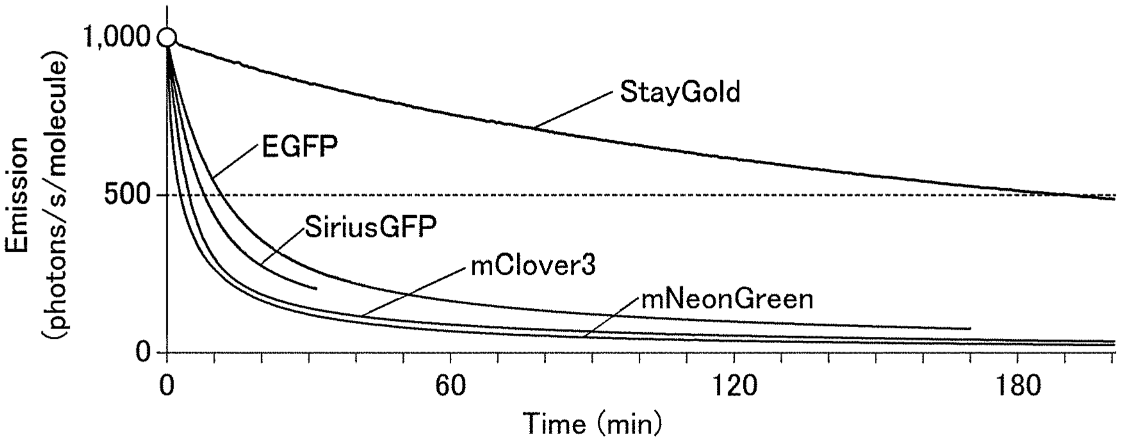
FIG. 6 is a diagram illustrating normalized fading curves of the five kinds of fluorescent proteins, for the case of using purified proteins, in accordance with Examples of the present invention.

FIG. 6 is a diagram illustrating normalized fading curves of the five kinds of fluorescent proteins, for the case of using purified proteins. For each of the fluorescent proteins, a time ($t_{1/2}$) required for a fluorescence emission rate to decrease from 1,000 photons/s per molecule, which was the rate at the start of the measurement, to 500 photons/s per molecule was calculated (Table 1). EGFP exhibited a higher $t_{1/2}$ value, which was 700 s, than any of the other publicly known fluorescent proteins. However, StayGold largely surpassed this, and exhibited a value of more than 10,000 s. These results shows that StayGold has photostability which is not less than 10 times as high as those of the other fluorescent proteins, i.e., StayGold is capable of emitting a number of photons until fading occurs, the number being not less than 10 time as many as those of the other fluorescent proteins.

(7-2. Comparison with Fluorescent Proteins of Different Colors)

Furthermore, a comparison of photostability was made between StayGold and each of 15 fluorescent proteins which are: EGFP, SiriusGFP, mNeonGreen, mClover3, TagRFP-T, mOrange2, mScarlet-H, mCardinal, mCherry, mScarlet-I, mTFP1, Venus, Achilles, mGold, and mVenus.

In these 20 years, several robust fluorescent proteins such as TagRFP-T, mOrange2, and mScarlet-H have been developed. Fluorescent proteins of red and orange have mainly been improved in terms of photostability. Although it is impossible to make a direct comparison between fluorescent proteins of different colors, it is possible to carry out a standard method to make quantitative comparison and evaluation of fading characteristic based on the calculation of $t_{1/2}$.

(Materials and Method)

The same method that was carried out in (7-1. Comparisons with green fluorescent proteins) was used.

(Result)

Figure 7:
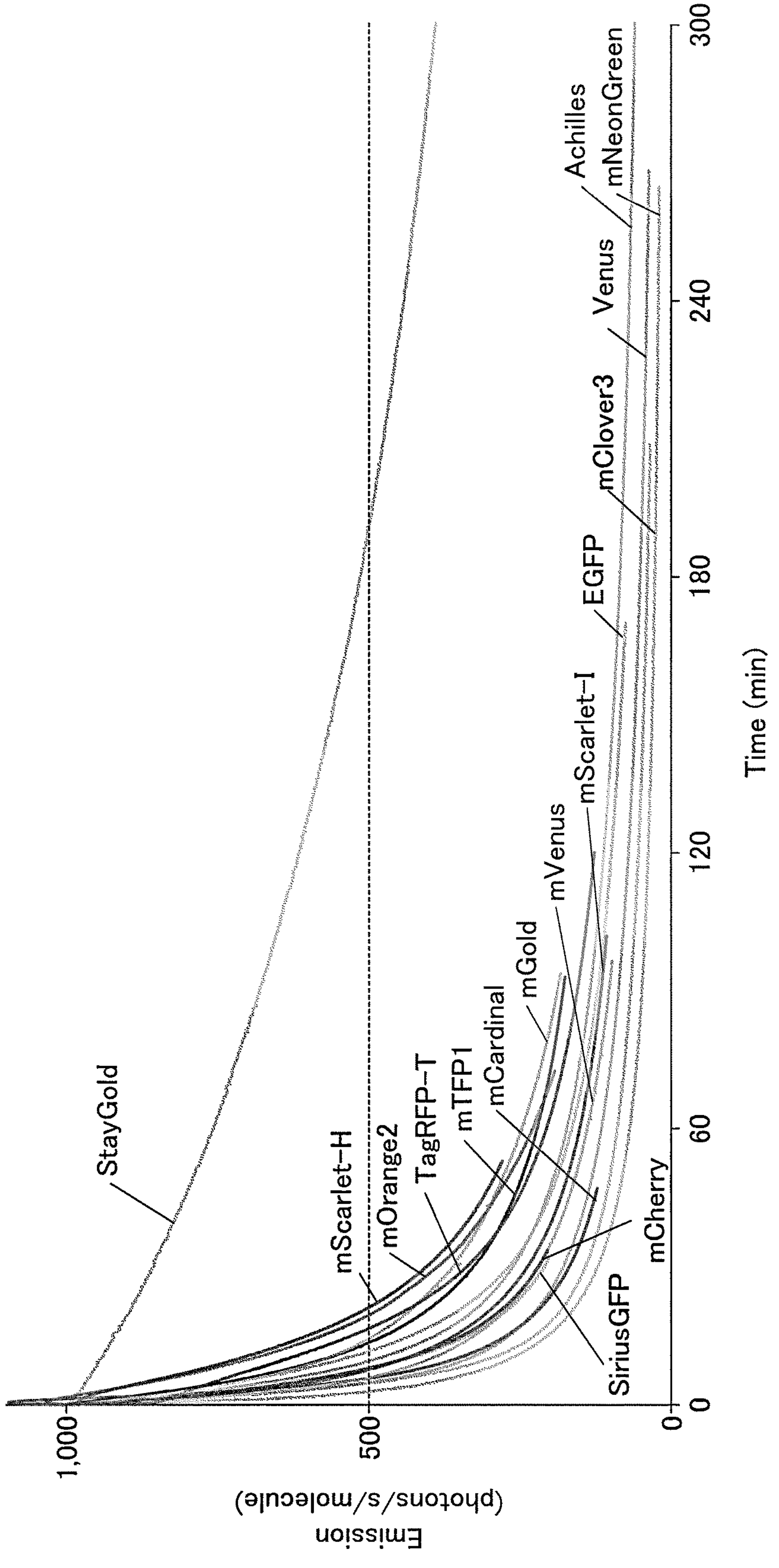
FIG. 7 is a diagram illustrating normalized fading curves of 16 kinds of fluorescent proteins, in accordance with Examples of the present invention.

FIG. 7 is a diagram illustrating normalized fading curves of a total of 16 kinds of fluorescent proteins which are StayGold and 15 fluorescent proteins. As shown in FIG. 7, StayGold had an advantage over the other fluorescent proteins having been investigated, in term of performance.

8. Analysis of Photobleach Characteristic of StayGold (Living Cell)

With use of living cells, a comparison of photobleach characteristic was made between StayGold and each of four green fluorescent proteins which are: EGFP, SiriusGFP, mNeonGreen, and mClover3.

(Materials and Method)

By carrying out lentivirus vector gene introduction, a HeLa cell which stably expressed each of the fluorescent proteins throughout the cell was prepared. The cell was cultured in a 35 mm glass bottomed dish. A change in fluorescence intensity associated with fading was measured with use of a fluorescence microscope (IX81, Olympus) and an image analysis device (AQUACOSMOS, Hamamatsu Photonics). As an excitation light source, a xenon lamp (75 W) was used. The excitation wavelength was adjusted via a band-pass filter to have a center wavelength of 488 nm and a half-value breadth of 10 nm, and this excitation light was applied, through an objective lens (UPlanSApo 40×, numerical aperture: 0.95), to a cell sample placed on a stage. A fluorescent image of the cell was captured on a cooled CCD camera (ORCA-AG, Hamamatsu Photonics) through a 520 nm long pass filter. The excitation light was applied continuously for 60 minutes, and an image of fluorescence was captured every 6 seconds. The average of the luminances of 20×20 pixels in the cell was determined from the obtained image, and from this determined average, a luminance of a portion containing no cell was subtracted as background light. By plotting the cell luminances of the respective time points, an attenuation curve due to fading of fluorescence was obtained.

With use of a cultured living cell in which each of the five kinds of green fluorescent proteins was expressed, photostability with consideration for fluorescence brightness was investigated.

Figure 8:
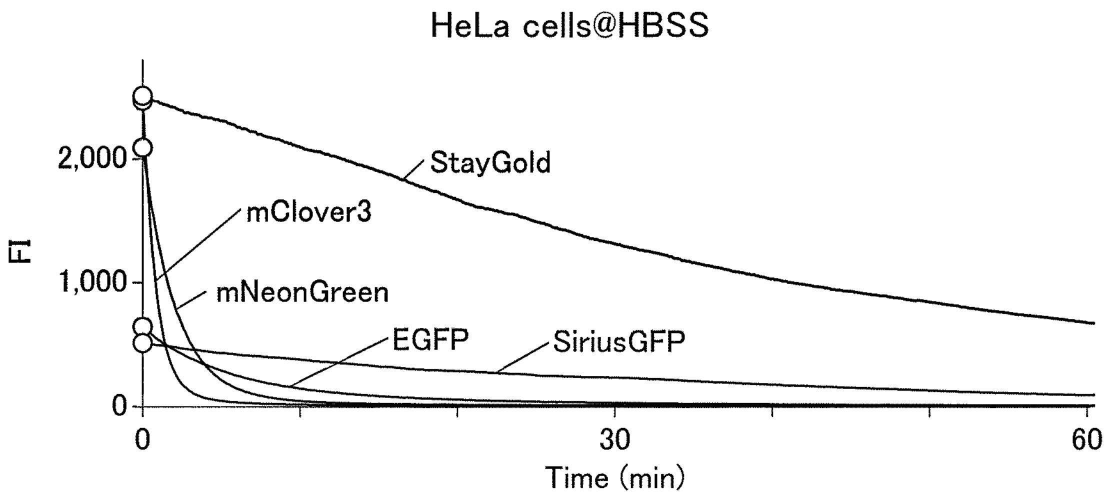
FIG. 8 is a diagram illustrating a simple comparison of a change in fluorescence intensity over time among five kinds of green fluorescent proteins in living cells, in accordance with Examples of the present invention.

FIG. 8 is a diagram illustrating a simple comparison of a change in fluorescence intensity over time among the five kinds of green fluorescent proteins in living cells.

Figure 9:
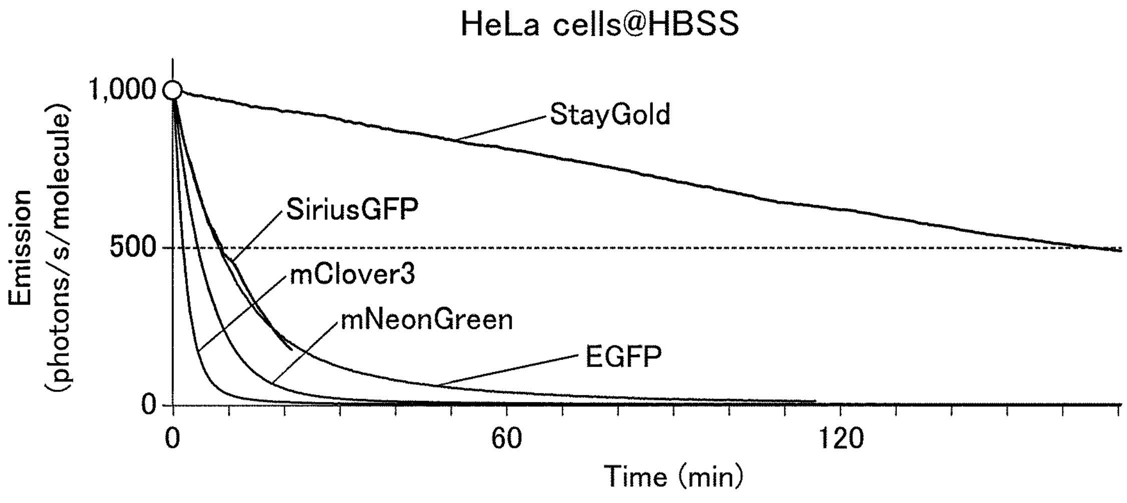
FIG. 9 is a diagram illustrating normalized fading curves of the five kinds of green fluorescent proteins in living cells, in accordance with Examples of the present invention.

FIG. 9 is a diagram illustrating normalized fading curves of the five kinds of green fluorescent proteins in living cells. Note that HBSS in FIGS. 8 and 9 means the Hank's balanced salt solution.

These results also have proved that StayGold has obvious photostability and excellent brightness. For example, the $t_{1/2}$ of StayGold was 9,919 s, whereas $t_{1/2}$ of Sirius GPF, which was the highest of those of the other fluorescent proteins, was 522 s (Table 1). Although not illustrated, the case in which the living cells were incubated with use of DMEM instead of HBSS indicated the same tendency. Specifically, the $t_{1/2}$ of Sirius GPF, which was the highest of those of the other fluorescent proteins, was 558 s, whereas the $t_{1/2}$ of StayGold was more than 10,000 s. As above, it has been found that StayGold has photostability which is not less than one or two orders of magnitude greater than those of any other conventionally, publicly known fluorescent proteins currently available.

9. Analysis of Photobleach Characteristic of StayGold (Cell Observation)

In order for a direct comparison of photobleach to be made in a single field of view, a StayGold expressing cell and an EGFP expressing cell were mixed together for observation. Further, one-to-one comparison was made in the same manner between a StayGold expressing cell and an mNeonGreen expressing cell.

(Materials and Method)

By carrying out lentivirus vector gene introduction, a HeLa cell which stably expressed each of the fluorescent proteins throughout the cell was prepared. The StayGold expressing cell and the EGFP expressing cell were mixed together or the StayGold expressing cell and the mNeonGreen expressing cell were mixed together, and the mixture was cultured in a 35 mm glass bottomed dish. The course of fluorescence fading was recorded with use of a fluorescence microscope (IX81, Olympus) and an image analysis device (AQUACOSMOS, Hamamatsu Photonics). As an excitation light source, a xenon lamp (75 W) was used. The excitation wavelength was adjusted via a band-pass filter to have a center wavelength of 488 nm and a half-value breadth of 10 nm, and this excitation light was applied, through an objective lens (UPlanSApo 60×, numerical aperture: 1.35), to a cell sample placed on a stage. A fluorescent image of the cell was captured on a cooled CCD camera (ORCA-AG, Hamamatsu Photonics) through a 520 nm long pass filter. The excitation light was applied continuously for 30 minutes, and an image of fluorescence was captured every 6 seconds.

(Result)

Figure 10:
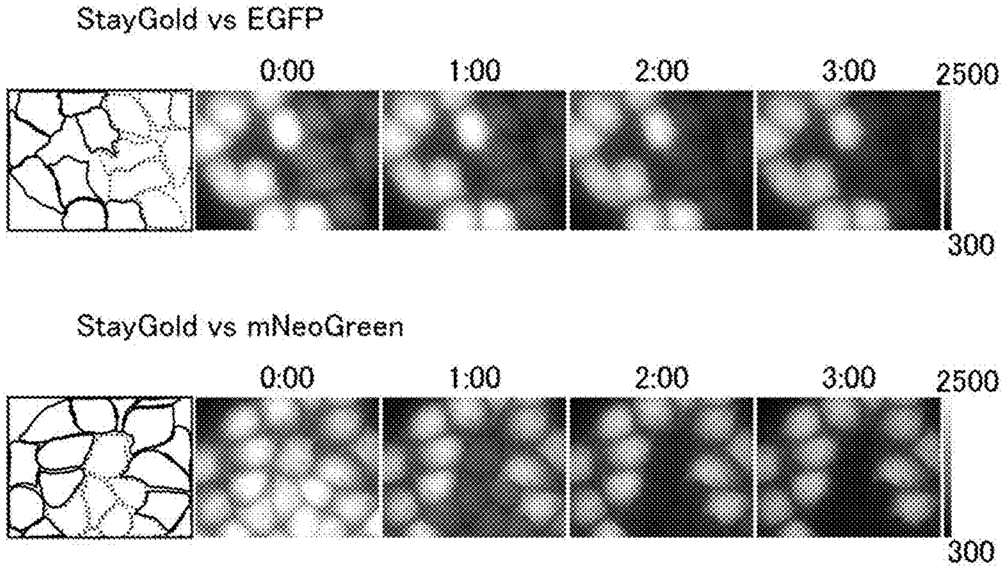
FIG. 10 illustrates a comparison of photobleach between a StayGold expressing cell and an EGFP expressing cell and a comparison of photobleach between a StayGold expressing cell and an mNeonGreen expressing cell, in accordance with Examples of the present invention.

FIG. 10 illustrates a comparison of photobleach between the StayGold expressing cell and the EGFP expressing cell and a comparison of photobleach between the StayGold expressing cell and the mNeonGreen expressing cell.

From the results shown in FIG. 10, StayGold has been proved to be brighter and have higher photostability than EGFP.

It should be noted that in the comparative experiment on the StayGold expressing cell and the mNeonGreen expressing cell, because the two cell groups have the same initial fluorescence intensity, it is thus impossible to discriminate between the two cell groups at t=0. Also in separate cell culture experiments carried out with use of cDNA transfection, it was observed that StayGold matured at a maturation rate which was equivalent to that of mNeonGreen, which is substantially the brightest-ever fluorescent protein.

In most cases, an oxygen molecule is considered to act on a fluorescent protein in both ways. On one hand, an oxidation reaction due to attack by oxygen molecules is necessary for a chromophore to mature, and what contributes to a substantial increase in brightness is the level of oxygen binding degree. On the other hand, degradation of a fluorescence chromophore is caused by attack by oxygen molecules which occurs during a stay in the excited-state, and the level of oxygen binding degree therefore acts so as to reduce photostability.

Fluorescence fading experiments were carried out with use of a fluorescent protein expressing cell under not only a normal oxygen condition but also an oxygen-free condition and a hyperoxic condition (not illustrated). As a result, like EGFP, SiriusGFP, mClover3, and mNeonGreen, StayGold was also found to have oxygen sensitivity.

10. Preparation of Tandem Dimer of StayGold Mutant (Materials and Method)

From the sequence of StayGold, a tandem dimer of a StayGold mutant was prepared.

(Result)

A tandem dimer protein which has two amino acid sequences of the StayGold mutant linked together therein was obtained. Two kinds of tandem dimer proteins of different structures were obtained.

The two kinds of tandem dimer proteins were expressed in *Escherichia coli* and purified by the same method for CU17S and StayGold described above. As a result, for each of the two kinds, a huge amount of tandem dimer proteins were successfully produced and purified. The two respective kinds of proteins were named tdStayGold and tdStayGold (long). The amino acid sequence of tdStayGold is indicated in SEQ ID NO: 13, and the base sequence of a coding region of tdStayGold is indicated in SEQ ID NO: 14. The amino acid sequence of tdStayGold (long) is indicated in SEQ ID NO: 15 and the base sequence of a coding region of tdStayGold (long) is indicated in SEQ ID NO: 16.

In either of the tandem dimer proteins, two sequences of the StayGold mutant are linked together via an insertion sequence of 132 amino acids. In addition, tdStayGold (long) has c4 (10 amino acids, SEQ ID NO: 8) further added to the C terminus of tdStayGold therein.

It has been found that tdStayGold is suitably used to be fused with the C terminus of a certain protein X. In that case, the fusion protein has a structure of protein X-tdStayGold. It has also been found that tdStayGold (long) is suitably used to be fused with the N terminus of a certain protein X. In that case, the fusion protein has a structure of tdStayGold (long)-protein X.

12. Microtubule Labeling with Tandem Dimer of StayGold Mutant

An expression construct was prepared, the expression construct encoding a fusion protein which had the C terminus of a human wild-type tau four-repeat (hereinafter referred to simply as "Tau") linked to the N terminus of tdStayGold therein with use of a Gly-Gly linker, the tdStayGold having the amino acids of SEQ ID NO: 13, the Tau being a microtubule binding protein.

Into a HeLa cell, 1 ug of plasmid DNA (Tau-GG-tdStayGold/pcDNA3) was introduced with use of Lipofectamine 2000, and one day after the introduction, the fluorescence of a living cell was observed. The observation was carried out via a confocal laser scanning microscope (FV3000). The objective lens: UPLSAPO 60XS/1.3 NA, Sampling speed: 2.0 μs/pixel, Integrations in line: three times, Zoom: 3×, C.A.: 222 nm, Laser light: 488 nm, 1.5%, PMT potential: 520 V, Detection: 500 nm to 600 nm.

(Result)

Figure 11:
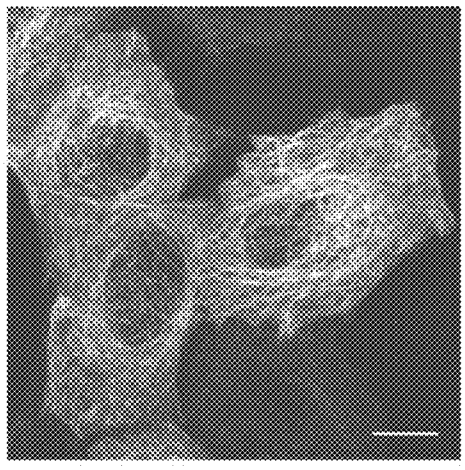
FIG. 11 is a view illustrating the result of labeling microtubules with tdStayGold, in accordance with Examples of the present invention.

FIG. 11 is a view illustrating the result of labeling microtubules with tdStayGold (in FIG. 11, the scale bar represents 10 μm). As illustrated in FIG. 11, tdStayGold caused microtubules in a cell to be labeled brightly. In addition, it was found that the fluorescence of tdStayGold did not fade, and tdStayGold therefore made it possible to clearly observe the dynamics of a microtubule in a living cell 13. Golgi Apparatus Membrane Protein Labeling with Tandem Dimer of StayGold Mutant By adding an insertion sequence c4 (10 amino acids, SEQ ID NO: 8) at the C terminus of the amino acid sequence of a StayGold tandem dimer used in Example 12, tdStayGold (long) having the amino acid sequence of SEQ ID NO: 15 was prepared. The base sequence of a coding region of tdStayGold (long) having the amino acid sequence of SEQ ID NO: 15 is indicated in SEQ ID NO: 16.

An expression construct was prepared, the expression construct encoding a fusion protein which was targeted at the membrane of the Golgi apparatus and which had the N terminus of the amino acid sequence (a sequence of No. 3131 to No. 3259 of the amino acid sequence of a Giantin protein of a human) of a membrane protein Giantin of the Golgi apparatus linked to the C terminus of tdStayGold (long) therein, the tdStayGold having the amino acid sequence of SEQ ID NO: 15. The construct was introduced into a HeLa cell, a fluorescent protein was thus transiently expressed, and fluorescence of a living cell was observed.

Into a HeLa cell, 1 ug of plasmid DNA (tdStayGold (long)-Coupler-Giantin/pcDNA3) was introduced with use of Lipofectamine 2000. One day after the introduction, observation was carried out via a super-resolution microscope SpinSR10. Camera: ORCA-Flash4.0, Objective lens: UPLAPO OHR 100×, NA=1.5, CSU disk: SoRa, Magnification: 3.2×, Laser light: 488 nm, 1%, Exposure time: 100 msec, Z steps: 0.25 um/slice, 46 slices, DM: D405/488/561/640, CH1 Filter Wheel: B525/50, B525/50, Buffer: HBSS, 10 mM HEPES-NaOH (pH7.4).

(Result)

Figure 12:
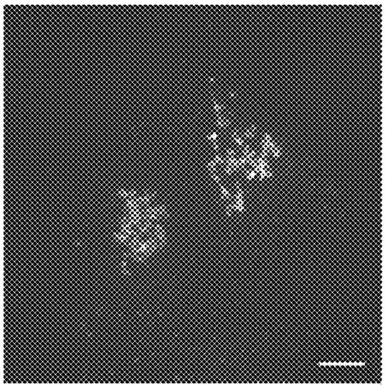
FIG. 12 is a view illustrating the result of labeling the membrane of the Golgi apparatus with tdStayGold (long), in accordance with Examples of the present invention.

FIG. 12 is a view illustrating the result of labeling the membrane of the Golgi apparatus with tdStayGold (long) (in FIG. 12, the scale bar represents 5 μm). As illustrated in FIG. 12, tdStayGold (long) caused the membrane of the Golgi apparatus in a cell to be labeled brightly. It has therefore been found that it is possible to observe the dynamics of the membrane of the Golgi apparatus in a living cell at high resolution, at high speed, continuously, and without fading.

14. Postsynaptic Protein PSD-95 Labeling with Tandem Dimer of StayGold Mutant

StayGold contained in StayGold tandem dimer having the amino acid sequence of SEQ ID NO: 13 underwent further mutations of H169Y, C174I, and C208I so that a StayGold mutant (oxStayGold) was prepared. From the sequence of oxStayGold, an oxStayGold tandem dimer (tdoxStayGold) having the following structure was prepared.

tdoxStayGold: (n1)oxStayGold(c4)-EV linker-(n1)oxStayGold

The amino acid sequence of tdoxStayGold is indicated in SEQ ID NO: 17, and the base sequence of a coding region of tdoxStayGold is indicated in SEQ ID NO: 18.

An expression construct was prepared, the expression construct encoding a fusion protein (PSD-95-Coupler-tdoxStayGold) which had the C terminus of a postsynaptic protein PSD-95 linked to the N terminus of tdoxStayGold therein, the fusion protein was expressed in a primary-cultured nerve cell of the hippocampus of a rat fetus, and fluorescence of a living cell was observed. Note that Coupler linker is a linker which had three repetitions of Gly-Gly-Gly-Gly-Ser sequence connected one after another therein.

Into the primary-cultured nerve cell (DIV4: the fourth day of in vitro culture) of the hippocampus of a rat fetus, 4 μg of plasmid DNA (PSD95-Coupler-tdoxStayGold/pcDNA3) was introduced with use of the calcium phosphate method. At DIV25 (the 25th day of in vitro culture) of the primary-cultured nerve cell, observation was carried out via a SpinSR10 microscope. Camera: ORCA-Flash4.0, Objective lens: UPLAPO OHR 100×, NA=1.5, CSU disk: 50 um, Zoom: ×1, Laser light: 488 nm, 10%, Excitation time: 500 msec, Z steps: 0.25 um/slice, 30 slices, DM: D405/488/561/640, CH1 Filter Wheel: B525/50, B447/60, Culture media at the time of image taking: DMEM/F12 (1:1), 2% FBS, N2-supplement (×1), B-27 (×1.5).

(Result)

Figure 13:
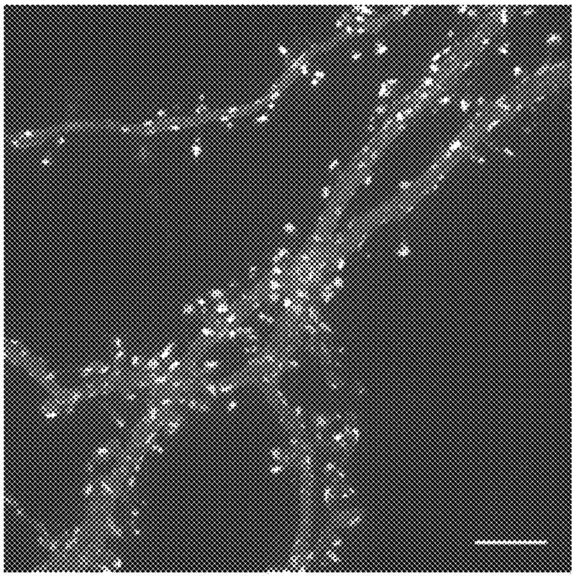
FIG. 13 is a view illustrating the result of carrying out labeling with a fusion protein of tdoxStayGold and PSD-95, which is a postsynaptic protein, in accordance with Examples of the present invention.

FIG. 13 is a view illustrating the result of labeling the protein PSD-95 with tdoxStayGold (in FIG. 13, the scale bar represents 20 μm). As illustrated in FIG. 13, labeling with tdoxStayGold made it possible to clearly observe the PSD-95 in the form of a liner structure, the PSD-95 being localized in a glutamic acid receptor adjusting signal plasticity and a signal molecule.

15. Endoplasmic Reticulum Membrane Labeling with Tandem Dimer StayGold Mutant

From the sequence of StayGold, a mutant tandem dimer (tdStayGold alpha) having the structure below was prepared.

tdStayGold alpha: (n1)StayGold(c4)-alpha linker-(n1)StayGold

The amino acid sequence of tdStayGold alpha is indicated in SEQ ID NO: 19, and the base sequence of a coding region of tdStayGold alpha is indicated in SEQ ID NO: 20.

By linking tdStayGold alpha to a protein called cytoplasmic end of an endoplasmic reticulum (ER) signal-anchor membrane protein (CytERM), an expression construct was prepared, the expression construct encoding a fusion protein targeted at the membrane of an endoplasmic reticulum. The construct was introduced into a HeLa cell, a fluorescent protein was thus transiently expressed, and fluorescence of a living cell was observed.

Into a HeLa cell, 1 ug of plasmid DNA (CytERM-tdStayGold alpha/pcDNA3) was introduced with use of Lipofectamine 2000. Observation was carried out via a widefield microscope (IX83 P2ZF). Camera: ORCA-Fusion, Objective lens: UPLXAPO 40×, NA=0.95, Cube: U-FBNA (excitation: 470 to 495, fluorescence: 510 to 550, DM: 505), Excitation light: 5%. ND filter: 10%, Excitation time: 500 msec, Buffer: HBSS, 10 mM HEPES-NaOH (pH7.4).

(Result)

Figure 14:
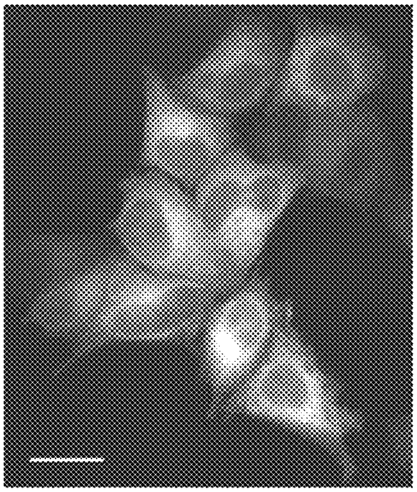
FIG. 14 is a view illustrating the result of labeling the membrane of an endoplasmic reticulum with tdStayGold alpha, in accordance with Examples of the present invention.

FIG. 14 is a view illustrating the result of labeling the membrane of an endoplasmic reticulum with tdStayGold alpha (in FIG. 14, the scale bar represents 20 μm).

When a fluorescent protein is linked to the C terminus of CytERM, the ER is labeled such that the membrane is pieced by the fluorescent protein from the cytoplasm-side. When the fluorescent protein forms a multimer, membranes overlap each other so that a vortex-like shape (bright points) appears.

In a case of linking N terminus of (n1)StayGold to the C terminus of CytERM, a number of such vortexes (bright points) appeared (not illustrated), the (n1)Stay Gold being obtained by inserting an insertion sequence n1 into the amino acid sequence of StayGold, which is the amino acid sequence of SEQ ID NO: 1. In contrast, as illustrated in FIG. 14, in a case of linking tdStayGold alpha, few vortexes appeared.

16. Endoplasmic Reticulum Inner Cavity Labeling with StayGold Mutant

A StayGold mutant ((n2)oxStayGold (c4)) which had insertion sequences n2 and c4 inserted in the amino acid sequence of oxStayGold therein was prepared.

On the basis of (n2)oxStayGold(c4), a StayGold mutant (er-(n2)oxStayGold(c4)) having the structure below was prepared.

er-(n2)oxStayGold(c4): SP(CRT)-(n2)StayGold(c4)-KDEL

The amino acid sequence of er-(n2)oxStayGold(c4) is indicated in SEQ ID NO: 21, and the base sequence of a coding region of er-(n2)oxStayGold(c4) is indicated in SEQ ID NO: 22. In this respect, SP(CRT) was the sequence of a calreticulin signal peptide, and KDEL was the sequence of an ER retention signal. A construct encoding er-(n2)oxStayGold(c4) was prepared, a fusion protein was transiently expressed in a HeLa cell, and fluorescence of a living cell was observed.

Plasmid DNA was introduced in a HeLa cell with use of PEI. Observation was carried out via a super-resolution microscope N-SIM S. Camera: ORCA-Fusion, Objective lens: SR HP Plan Apo 100×/1.35 Sil λS, Image capturing mode: 3D-SIM, Laser light: 488 nm, 50%, Excitation time: 15 msec, Buffer: HBSS, 10 mM HEPES-NaOH (pH7.4).

(Result)

Figure 15:
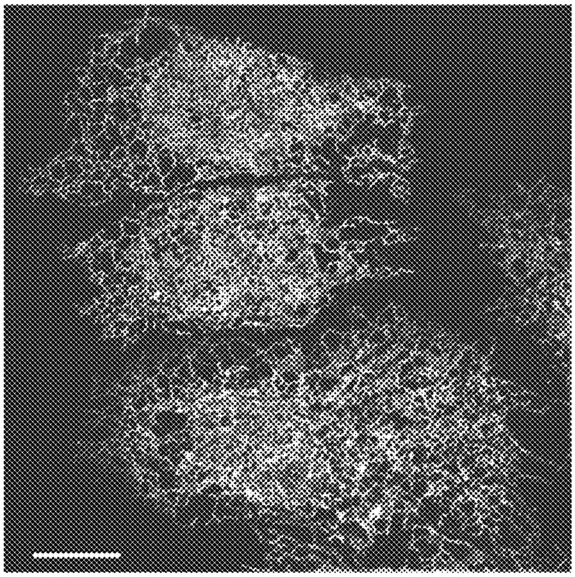
FIG. 15 is a view illustrating the result of labeling the inner cavity of an endoplasmic reticulum with er-(n2) oxStayGold(c4), in accordance with Examples of the present invention.

FIG. 15 is a view illustrating the result of labeling the inner cavity of an endoplasmic reticulum with er-(n2)oxStayGold(c4) (in FIG. 15, the scale bar represents 10 μm). As illustrated in FIG. 15, er-(n2)oxStayGold(c4) caused the inner cavity of an endoplasmic reticulum in a cell to be labeled brightly. It has therefore been found that it is possible to observe the dynamics of the inner cavity of an endoplasmic reticulum in a living cell at high resolution, at high speed, continuously, and without fading.

17. Mitochondria Membrane Labeling with StayGold Mutant

With use of StayGold having the amino acid sequence of SEQ ID NO: 1, mt-StayGold was prepared, which has the configuration below.

mt-StayGold: CoxVIII×2-StayGold

The amino acid sequence of mt-StayGold is indicated in SEQ ID NO: 23, and the base sequence of a coding region of mt-StayGold is indicated in SEQ ID NO: 24. In this respect, CoxVIII(cytochrome c oxidase subunit VIII) was the sequence to be transported into mitochondria. With use of an expression construct encoding a fusion protein in which an amino acid sequence (the number of amino acids is 72, amino acids 1 to 72 of SEQ ID NO: 23) which is two repetitions of the sequence of CoxVIII was bound to the N terminus-side of the amino acid sequence (amino acids 75 to 291 of SEQ ID NO: 23) of StayGold, mt-StayGold was prepared. Note that amino acids 73 and 74 of SEQ ID NO: 23 consist of a sequence derived from BamHI that had been used at the time of preparation of mt-StayGold.

This gene was incorporated into plasmid (CSII-EF-MCS) for cell expression, and a HeLa cell was transfected so that mt-StayGold was expressed. As a result, it was found that mt-StayGold emitted fluorescence in mitochondria (not illustrated). Further, with use of a lentivirus, a HeLa cell which stably expressed mt-StayGold was prepared. Even in a case where a lentivirus was used, mt-StayGold that emitted fluorescence was successfully obtained (not illustrated).

As a fluorescent protein having a fluorescence intensity which was improved upon mt-StayGold, mt-(n1)StayGold having the configuration below was prepared by inserting an insertion sequence n1 (9 amino acids) between amino acids 4 and 5 of the amino acid sequence of StayGold (SEQ ID NO: 1) in the amino acid sequence of SEQ ID NO: 23.

mt-(n1)StayGold: CoxVIII×2-(n1)StayGold

The amino acid sequence of mt-(n1)StayGold is indicated in SEQ ID NO: 25, and the base sequence of a coding region of mt-(n1)StayGold is indicated in SEQ ID NO: 26.

Plasmid DNA was introduced into a HeLa cell with use of a lentivirus. An image of the HeLa cell after the introduction of mt-(n1)StayGold was captured with use of a fluorescence microscope (IX81, Olympus) and an image analysis device (AQUACOSMOS, Hamamatsu Photonics).

Excitation wavelength: 460 nm to 495 nm, Fluorescence wavelength: 510 nm, Long pass dichroic mirror: 505 nm, Objective lens: UPlanSApo 60×, NA 1.35, Cooled CCD camera: ORCA-AG, Binning: 2×2, Exposure time: 90 ms.

(Result)

Figure 16:
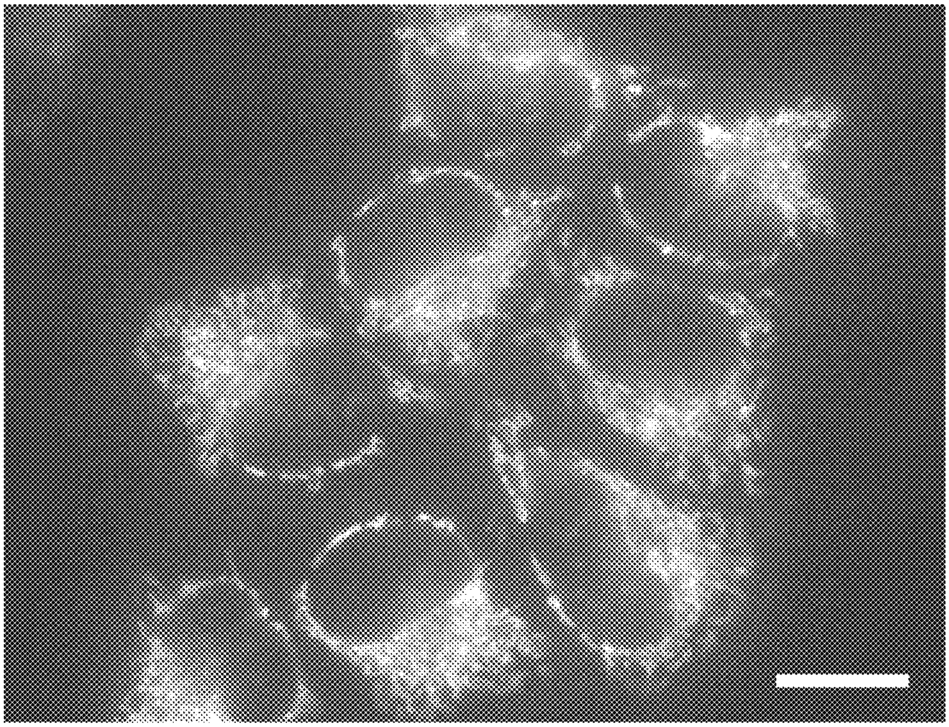
FIG. 16 is a view illustrating the result of labeling mitochondria with mt(n1)-StayGold, in accordance with Examples of the present invention.

FIG. 16 is a view illustrating the result of labeling mitochondria with mt-(n1)StayGold (in FIG. 16, the scale bar represents 20 μm). The mt-(n1)StayGold enabled mitochondria to be labeled brightly, and therefore made possible high-speed, long-duration imaging.

18. Monomerization of StayGold Mutant (1) Consideration of Y187A Mutation and L155T Mutation StayGold of SEQ ID NO: 1 underwent a mutation of Y187A or L155T so that a StayGold mutant (StayGold Y187A, StayGold L115T) was prepared. The amino acid sequence of StayGold Y187A is indicated in SEQ ID NO: 27, and the base sequence of a coding region of StayGold Y187A is indicated in SEQ ID NO: 28. The amino acid sequence of StayGold L115T is indicated in SEQ ID NO: 29, and the base sequence of a coding region of StayGold L1 15T is indicated in SEQ ID NO: 30.

As illustrated in Table 2, recombinant proteins were prepared through *Escherichia coli* JM109 DE3, with use of expression constructs encoding StayGold mutants, StayGold (dimer), and EGFP (monomer). After purification of the proteins with use of Ni-NTA, pseudo-native PAGE was carried out. The separation gel contained 10% acrylamide and 0.1% SDS. The sample buffer contained 2% SDS and 100 mM DTT. No heat treatment was carried out.

TABLE 2

| Number | Fluorescent protein |
|---|---|
| 1 | StayGold Y187A |
| 2 | StayGold L155T |
| 3 | StayGold (dimer) |
| 4 | EGFP (monomer) |

(Result)

Figure 17:
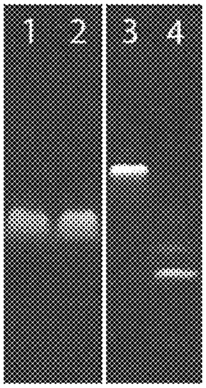
FIG. 17 a view illustrating the result of pseudo-native PAGE regarding a StayGold mutant which has a mutation of L155T or Y187A introduced therein, in accordance with Examples of the present invention.

FIG. 17 provides the results. As illustrated in FIG. 17, a possibility that StayGold Y187A and StayGold L155T were monomers was indicated.

(2) Consideration of Further Mutation

A StayGold mutant ((n1)oxStayGold) was prepared, the StayGold mutant having further insertion of the insertion sequence n1 performed on oxStayGold prepared in Example 14. By introducing a mutation into (n1)oxStayGold/pRSET through Site Directed Mutagenesis, an (n1)oxStayGold mutant having the amino acid sequence of SEQ ID NO: 31 was prepared ((n1)oxStayGold L155T). The base sequence of a region encoding (n1)oxStayGold L155T is indicated in SEQ ID NO: 32. The mutant (n1)oxStayGold L155T underwent further mutation based on the original crystal structure of StayGold. Table 3 provides mutations undergone by (n1)oxStayGold L155T and fluorescent proteins (AzamiGreen (tetramer), EGFP (monomer), and StayGold (dimer)) used as Comparative Examples. Note that the positions of amino acid replacements indicated in Table 3 correspond to the positions of amino acids in the amino acid sequence of StayGold (SEQ ID NO: 1) that does not contain an insertion sequence n1. Furthermore, the (n1)oxStayGold mutants of 1, 2, and 7 to 12 in Table 3 were mutants having mutations of, in the amino acid sequence of StayGold (SEQ ID NO: 1), replacing asparagine of amino acid 132 with asparagine acid (N132D), replacing proline of amino acid 151 with threonine (P151T), and replacing lysin of amino acid 162 with glutamic acid (K162E). In addition, the reason for selecting each of the mutations undergone by (n1)oxStayGold L155T is also provided in Table 3. Recombinant proteins were prepared through *Escherichia coli* JM109 DE3, with use of expression constructs encoding the (n1)oxStayGold mutants, AzamiGreen (tetramer), EGFP (monomer), and StayGold (dimer), as indicated in Table 3. After purification of the proteins with use of Ni-NTA, pseudo-native PAGE was carried out. The separation gel contained 10% acrylamide and 0.1% SDS. The sample buffer contained 2% SDS, 100 mM DTT. No heat treatment was carried out.

TABLE 3

| Number | Fluorescent protein | Reason for selection of mutation |
|---|---|---|
| 1 | (n1)oxStayGold L155T + L135T | Facing Y187 |
| 2 | (n1)oxStayGold L155T + P136Y | Facing Y187 |
| 3 | AzamiGreen (tetramer) | — |
| 4 | EGFP (monomer) | — |
| 5 | StayGold (dimer) | — |
| 6 | StayGold, I115T | — |
| 7 | (n1)oxStayGold L155T + I142T | Facing L155 |
| 8 | (n1)oxStayGold L155T + C165Q | Predicted to be important for monomerization |
| 9 | (n1)oxStayGold L155T + E138Q | E138s face each other in dimer of StayGold |
| 10 | (n1)oxStayGold L155T + W189Y | Predicted to be important for monomerization |
| 11 | (n1)oxStayGold L155T + R144T | Predicted to be important for monomerization (facing E167) |
| 12 | (n1)oxStayGold L155T + E167A | Predicted to be important for monomerization (facing R144) |

(Result)

Figure 18:
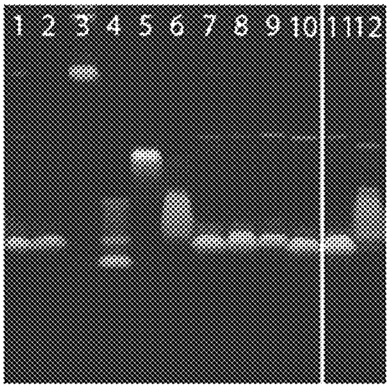
FIG. 18 is a view illustrating the result of pseudo-native PAGE regrading a StayGold mutant obtained by introducing a further mutation into the StayGold mutant which has the L155T mutation therein, in accordance with Examples of the present invention.

FIG. 18 provides the results. As shown in Table 18, the possibility that the (n1)oxStayGold L155T mutants listed in Table 2 are monomers has been indicated, in particular, it has been suggested that 1, 2, 7, 8, 9, 10, and 11 in Table 2 and FIG. 18 are mutations useful for monomerization.

19. Conclusion

As has been indicated above, the StayGold mutants emitted bright fluorescence and were significantly excellent in photostability. Until now, the improvement in photostability of fluorescent proteins have always entailed a reduction in brightness. The fluorescence property of StayGold was found to be different from the property of conventional fluorescent proteins, which is incompatibility between brightness and photostability.

INDUSTRIAL APPLICABILITY

An example of the fluorescent protein of the present invention emits bright fluorescence and has excellent photostability, and is therefore useful in a wide range of fields such as, for example, the molecular biology filed, the biochemical analysis field, and the medical field.

The invention claimed is:

1. A polypeptide having a fluorescence property, the polypeptide comprising any one of (1) to (3) below:

(1) a polypeptide having the amino acid sequence set forth in SEQ ID NO: 1;

(2) a polypeptide having the amino acid sequence set forth in SEQ ID NO: 1, the amino acid sequence having replaced, deleted, inserted, and/or added therein not less than 1 and not more than 32 amino acids, wherein amino acid 168 is an alanine and which is not permitted to be substituted; and (3) a polypeptide having not less than 85% sequence identity with respect to the amino acid sequence set forth in SEQ ID NO: 1, wherein amino acid 168 is an alanine and which is not permitted to be substituted.

2. The polypeptide according to claim 1, wherein the polypeptide exhibits higher photostability than EGFP or has brighter fluorescence than EGFP.

3. A polynucleotide indicated in any one of (1) to (3) below:

(1) a polynucleotide which encodes a polypeptide having the amino acid sequence set forth in SEQ ID NO: 1;

(2) a polynucleotide which encodes a polypeptide having the amino acid sequence set forth in SEQ ID NO: 1, the amino acid sequence having replaced, deleted, inserted, and/or added therein not less than 1 and not more than 32 amino acids, the polypeptide having a fluorescence property, wherein amino acid 168 is an alanine and which is not permitted to be substituted; and (3) a polynucleotide which encodes a polypeptide having not less than 85% sequence identity with respect to the amino acid sequence set forth in SEQ ID NO: 1 and having a fluorescence property, wherein amino acid 168 is an alanine and which is not permitted to be substituted.

4. An expression cassette comprising:

(a) an expression regulatory region functional in an expression host; and (b) the polynucleotide according to claim 3.

5. A vector comprising:

the polynucleotide according to claim 3.

6. A transformant comprising:

the polynucleotide according to claim 3.

7. The transformant according to claim 6, wherein the transformant is a non-human transgenic organism.

8. A fusion polypeptide comprising:

the polypeptide according to claim 1; and another polypeptide.

9. A fusion polypeptide comprising:

a polypeptide having a fluorescence property; and another polypeptide, the fusion polypeptide including not less than two polypeptides linked together each of which is a polypeptide indicated in any one of (1) to (3) below:

(1) a polypeptide having the amino acid sequence set forth in SEQ ID NO: 1;

(2) a polypeptide having the amino acid sequence set forth in SEQ ID NO: 1, the amino acid sequence having replaced, deleted, inserted, and/or added therein not less than 1 and not more than 32 amino acids, wherein amino acid 168 is an alanine and which is not permitted to be substituted; and (3) a polypeptide having not less than 85% sequence identity with respect to the amino acid sequence set forth in SEQ ID NO: 1, wherein amino acid 168 is an alanine and which is not permitted to be substituted.

10. A kit comprising the polynucleotide according to claim 3.

11. A fluorescence observation method comprising:

a producing step of producing, in a cell, the polypeptide according to claim 1;

an excitation light irradiating step of irradiating the cell with excitation light; and an observing step of observing fluorescence originating from the polypeptide.

12. A fluorescence observation method comprising:

a producing step of producing, in a cell, the fusion polypeptide according to claim 8;

an excitation light irradiating step of irradiating the cell with excitation light; and an observing step of observing fluorescence originating from the fusion polypeptide.

13. A fluorescence observation method comprising:

a producing step of producing, in a cell, the fusion polypeptide according to claim 9;

an excitation light irradiating step of irradiating the cell with excitation light; and an observing step of observing fluorescence originating from the fusion polypeptide.

* * * * *